(12) United States Patent
Wiley

(10) Patent No.: US 8,685,898 B2
(45) Date of Patent: Apr. 1, 2014

(54) ADAPTIVE IMMUNITY PROFILING AND METHODS FOR GENERATION OF MONOCLONAL ANTIBODIES

(75) Inventor: Steven R. Wiley, Seattle, WA (US)

(73) Assignee: Imdaptive, Inc., Seattle, WA (US)

( * ) Notice: Subject to any disclaimer, the term of this patent is extended or adjusted under 35 U.S.C. 154(b) by 175 days.

(21) Appl. No.: 13/144,645

(22) PCT Filed: Jan. 15, 2010

(86) PCT No.: PCT/US2010/021264
§ 371 (c)(1),
(2), (4) Date: Sep. 21, 2011

(87) PCT Pub. No.: WO2010/083456
PCT Pub. Date: Jul. 22, 2010

(65) Prior Publication Data
US 2012/0015829 A1 Jan. 19, 2012

Related U.S. Application Data

(60) Provisional application No. 61/145,039, filed on Jan. 15, 2009.

(51) Int. Cl.
*C40B 50/06* (2006.01)
(52) U.S. Cl.
USPC .......................................................... 506/26

(58) Field of Classification Search
None
See application file for complete search history.

(56) References Cited

U.S. PATENT DOCUMENTS

| | | | |
|---|---|---|---|
| 5,189,147 | A | 2/1993 | Saito et al. |
| 5,506,126 | A | 4/1996 | Seed et al. |
| 5,627,052 | A | 5/1997 | Schrader |
| 6,919,434 | B1 | 7/2005 | Goto et al. |
| 7,148,040 | B2 | 12/2006 | Meagher et al. |
| 2007/0243564 | A1 | 10/2007 | Lawson et al. |

FOREIGN PATENT DOCUMENTS

EP 2 088 432 A1 8/2009

OTHER PUBLICATIONS

Supplementary European Search Report for European Application No. 10732172.1, May 29, 2012, 5 pages.
PCT International Search Report and Written Opinion, PCT Application No. PCT/US2010/021264, Apr. 14, 2010, seven pages.

*Primary Examiner* — Christian Boesen
(74) *Attorney, Agent, or Firm* — Fenwick & West LLP

(57) ABSTRACT

Methods are provided for producing monoclonal antibody candidates using adaptive immunity profiling. In some aspects, the method provides for the use of massively parallel signature sequencing.

15 Claims, 9 Drawing Sheets

Figure 3A

1: Overlay primer sequences onto raw sequences

2: Group by inter-primer sequences and decode primer barcodes to identify sample source

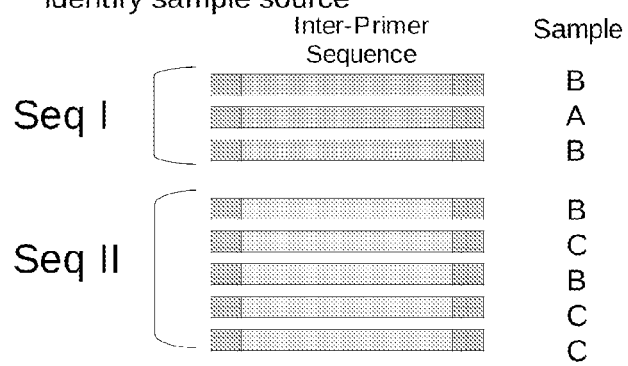

Seq I — Inter-Primer Sequence — Sample: B, A, B

Seq II — C, B, C, B, C, C

3: Create score-matrix for set of inter-primer sequences

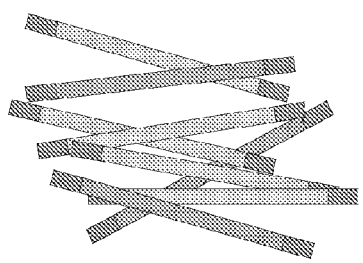

|  | Seq I | Seq II | ... | Seq N |
|---|---|---|---|---|
| Seq I |  | 344 | 356 | 238 |
| Seq II |  |  | 476 | 255 |
| ... |  |  |  | 183 |
| Seq N |  |  |  |  |

4: Create phylogenetic tree based on score matrix using algomerative clustering method; e.g. UPGMA

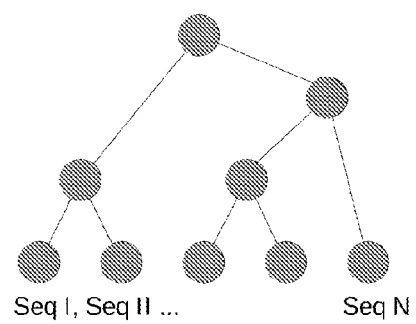

Seq I, Seq II ...    Seq N

5: Calculate e-score of foreground vs background sample set counts at each node.

6: Identify local peak nodes; lowest e-score (maximum specificity).

ADAPTIVE IMMUNITY PROFILING AND METHODS FOR GENERATION OF MONOCLONAL ANTIBODIES

CROSS REFERENCE TO RELATED APPLICATION

This application claims the benefit of U.S. Pat. App. No. 61/145,039, filed Jan. 15, 2009, which is hereby incorporated by reference in its entirety.

FIELD

The invention relates to the field of immunology, and in particular to adaptive immunity profiling and methods of producing monoclonal antibodies.

BACKGROUND

The existing methods for creating therapeutic monoclonal antibodies are primarily hybridoma, phage display, B cell isolation and antibody sequence rescue, followed if necessary by humanization of the antibody. The humanization step can be eliminated by using transgenic animals which are capable of themselves generating human antibodies.

The hybridoma method involves isolating large numbers of B cells from an immunized organism which are then fused with a myeloma tumor cell. These cells are then screened for individual cells producing antibodies with the desired properties. Once a particular hybridoma of interest is detected, a cDNA encoding the antibody is isolated and sequenced by standard molecular biology techniques, followed by a process of humanization. Humanization is the process of placing the variable region of the antibody, usually from a mouse or rabbit, into a human antibody backbone so that the resulting molecule is less immunogenic when used as a therapeutic agent in a human host. Hybridoma technology is limited by its low efficiency; the need for large numbers of B cells, which are generally obtained by sacrificing mice and harvesting from them splenic B cells; and the relative instability of the hybridomas themselves.

Phage display is a technology that uses a library of recombinant phage which present on their surface randomly paired variable domains of heavy and light chain antibodies taken from human donors. The phages are panned against the antigen of interest and those which specifically bind are amplified and the process is repeated. After multiple rounds of panning, representative phages' DNA are isolated and sequenced. The variable domains are then transferred into Ig constant region backbones. This technology often requires artificial affinity maturation in order to generate antibodies of sufficient affinity, which involves making a series of point mutations and retesting the affinity of the resulting antibodies. Moreover, the panning process is quite laborious and is often performed using robotics.

B cell isolation and antibody sequence rescue techniques involve isolating individual or small numbers of B cells and culturing them in vitro in order to create small amounts of conditioned supernatants which can be used to screen for antibodies with the desired properties. The selected lymphocyte antibody method (SLAM) is one aspect of this technology. Once an antibody with the desired properties is detected, the antibody's heavy and light chain are recovered from the cell or cells by standard molecular techniques such as PCR, and the resulting antibody is then humanized in the same manner as a hybridoma-derived antibody.

The methods currently available for the generation of monoclonal antibodies are laborious, time consuming, and subject to inaccuracy. Thus, there remains a need in the art for an efficient, easy, and accurate method for generating monoclonal antibodies.

SUMMARY

The present disclosure addresses long-felt needs in the field of immunology by providing a novel, efficient, and accurate method for producing high affinity monoclonal antibodies. The methods of the present disclosure are faster and less laborious than any existing technology for generating monoclonal antibodies. Using this method, sequence data can be generated in several days as compared to the weeks or months required by the other methods. Furthermore, since only small amounts of DNA are needed according to the present methods, data can be generated by non-invasive and non-lethal means which enables repeated sampling of the immunized organism and also allows the technique to be applied directly to human patients.

The adaptive immune system responds to changes in exposure of an organism to different pathogen and disease states by creating immune cells which are differentiated to respond to particular antigens. This occurs by genomic rearrangement at certain loci which in turn generates a wide variety of proteins not coded directly in the germline genomic DNA. Such regions subject to this kind of rearrangement include the Ig heavy and light chain variable domains, and the T-cell receptor alpha and beta variable domain regions. Once exposed to antigens which induce these changes, the cells which react to them will exist in the organism for years, and can rapidly proliferate in response to re-exposure to the antigen. In this way a record of antigen exposure is maintained in the host. This present disclosure describes a method to extract this information in order to create therapeutically useful monoclonal antibodies.

The present disclosure provides methods for producing monoclonal antibodies by applying new molecular and proteomic technologies with a novel method of data analysis.

Blood samples from immunized organisms are used to generate MPSS libraries profiling genes which are subject to rearrangement by the adaptive immune system, including but not limited to, the Ig heavy chain variable region.

According to one aspect, the present disclosure provides methods for producing monoclonal antibodies, the method comprising the steps of: (a) immunizing a host subject with an antigen; (b) creating a cDNA sequence library, the creating comprising the steps of: (i) isolating lymphocytes from the host subject, (ii) isolating mRNA from the lymphocytes, (iii) reverse transcribing the mRNA to cDNA, (iv) amplifying target antibody cDNA sequences, and (v) sequencing the target antibody cDNA sequences; and (c) analyzing the frequency of target antibody cDNA sequences, wherein target antibody cDNA sequences having a relatively high frequency are identified as candidate antibody sequences.

According to certain aspects, the lymphocytes comprise B cells and T cells. According to further aspects, the lymphocytes comprise isolated B cells. In some aspects, methods are provided wherein the relative frequencies of target antibody cDNA sequences are compared before and after exposure to the antigen, wherein target antibody cDNA sequences having a significantly higher frequency after exposure to the antigen are identified as candidate antibody sequences.

In further aspects, a host subject is re-immunized with the antigen, a cDNA sequence library is created after the re-immunization, and the relative frequencies of the target antibody sequences are compared before and after the re-immunization, wherein antibody sequences present at a significantly higher frequency after the re-immunization are identified as mature candidate antibody sequences.

In some aspects, methods are provided wherein the relative frequencies of target antibody cDNA sequences are compared at two or more times after exposure to the antigen, wherein target antibody cDNA sequences having a significantly lower frequency in later times are identified as candidate antibody sequences.

In some aspects, the target antibody sequences comprise immunoglobulin (Ig) heavy chain variable domain sequences. In further aspects the target antibody sequences comprise sequences of one or more complementarity determining regions (CDRs) of an immunoglobulin (Ig) heavy chain variable domain. In various aspects, a candidate antibody sequences with a light chain variable domain sequence and an Ig framework to produce a set of candidate monoclonal antibodies. In some aspects, the Ig framework is a human Ig framework.

According to certain aspects, the present disclosure provides methods for assaying the candidate monoclonal antibodies for affinity to an antigen. In further aspects, the present disclosure provides for subjecting the candidate monoclonal antibodies to positive selection to identify high affinity monoclonal antibodies. In yet further aspects, subjecting the candidate monoclonal antibodies to positive selection comprises contacting the candidate monoclonal antibodies to the antigen bound to a substrate and isolating bound antibodies from unbound antibodies. In certain aspects, the candidate monoclonal antibodies bind to an antigen with an affinity of at least $1 \times 10^{10}$ liter/mole, measured as an association constant ($K_{aff}$).

According to certain aspects, the present disclosure provides methods for sequencing the high affinity monoclonal antibodies. In further aspects, the relative frequencies of target antibody sequences are analyzed using a bioinformatics software algorithm. In yet further aspects the amplified target cDNA sequences are sequenced by massively parallel signature sequencing (MPSS).

In certain aspects, the host subject is an experimental animal. In some aspects, the host subject is a transgenic animal expressing human antibodies. In further aspects the host subject is a human patient that has been exposed to an antigen or a pathogen or is suffering from a disease which alters the adaptive immune response.

According to certain aspects, the present disclosure provides that a host subject is immunized with multiple antigens. In further aspects, the monoclonal antibody is reactive to multiple antigens.

According to certain aspects, the present disclosure provides methods for administering a background antigen and selecting against antibodies that are reactive to the background antigen. In further aspects, the background antigen is administered after a first antigen.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the disclosed subject matter.

DETAILED DESCRIPTION

Figure 1:
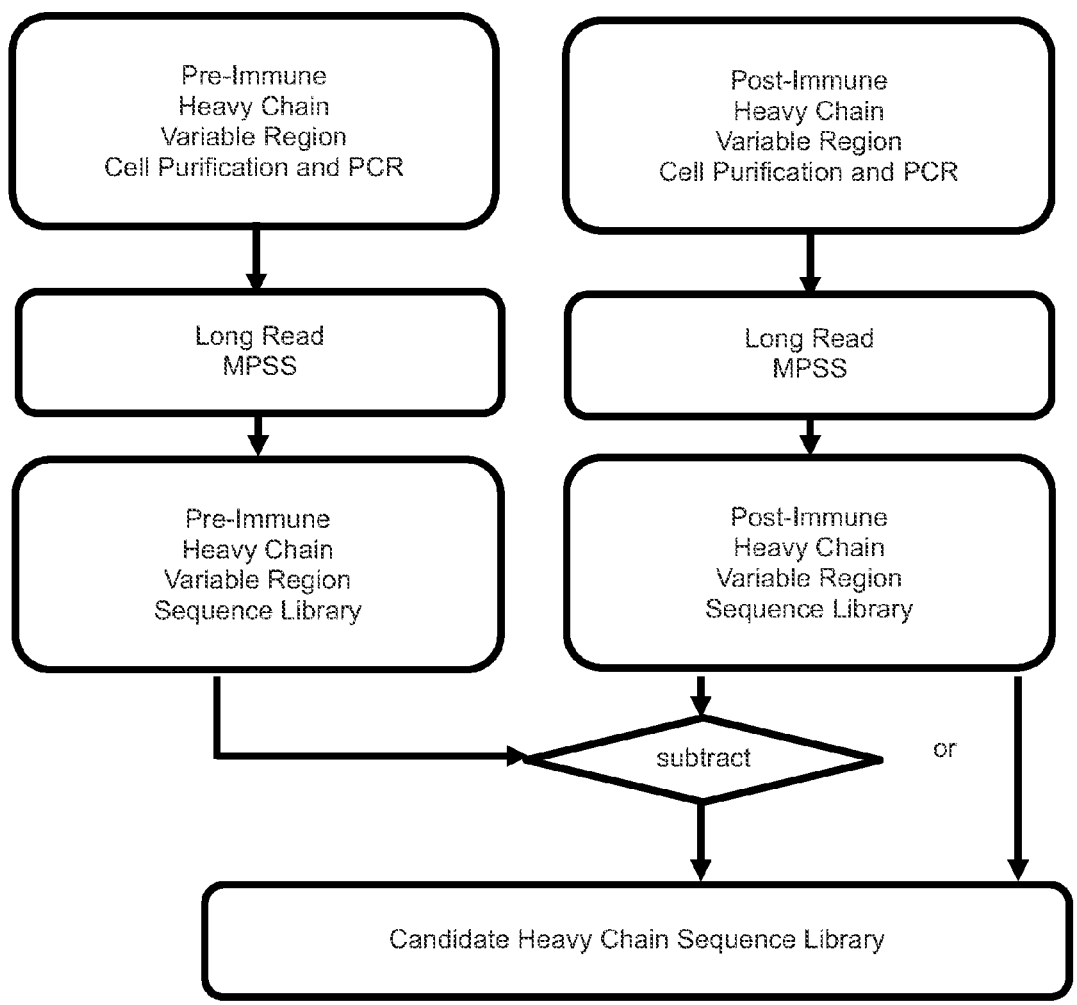
FIG. 1: Heavy Chain Sequence Library Generation. This figure illustrates an example process by which candidate antigen-specific variable chain regions can be generated. MPSS data is generated for a specific isotype of the Ig heavy chain variable region before and after exposure to antigen. These data are digitally analyzed in order to identify those sequences which have been generated in response to antigen exposure.

The present disclosure generally provides a novel, efficient, and accurate method for producing high affinity monoclonal antibodies. The methods of the present disclosure are faster and less laborious than any existing technology for generating monoclonal antibodies.

A person skilled in the art will appreciate that the present disclosure can be practiced without undue experimentation according to the methods given herein. The methods, techniques and chemicals are as described in the references given or from protocols in standard biotechnology and molecular biology textbooks.

The Figures and the following description relate to preferred aspects by way of illustration only. It should be noted that from the following discussion, alternative aspects disclosed herein will be readily recognized as viable alternatives that can be employed without departing from the principles of what is claimed.

It should be noted that the language used herein has been principally selected for readability and instructional purposes, and it can not have been selected to delineate or circumscribe the inventive subject matter. Accordingly, the disclosure is intended to be illustrative, but not limiting, of the scope of claimed methods.

As used in this specification and the appended claims, the singular forms "a", "an" and "the" include plural referents unless the content clearly dictates otherwise. Thus, for example, reference to "an antibody" includes a combination of two or more antibodies, and the like.

Any terms not directly defined herein shall be understood to have the meanings commonly associated with them as understood within the art of the present disclosure. Certain terms are discussed herein to provide additional guidance to the practitioner in describing the compositions, devices, methods and the like of aspects of the present disclosure, and how to make or use them. It will be appreciated that the same thing can be said in more than one way. Consequently, alternative language and synonyms can be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the aspects of the present disclosure herein.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Patient", "subject" or "mammal" are used interchangeably and refer to mammals such as human patients and non-human primates, as well as experimental animals such as rabbits, rats, and mice, and other animals. Animals include all vertebrates, e.g., mammals and non-mammals, such as sheep, dogs, cows, chickens, amphibians, and reptiles.

The term "sufficient amount" means an amount sufficient to produce a desired effect, e.g., an amount of antigen sufficient to give rise to an immune response in a host.

The term "isolated" means a biological component, such as a cell, group of cells, nucleic acid, peptide or protein, that has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been isolated thus include nucleic acids and proteins purified by standard purification methods. The term also embraces nucleic acids, peptides and proteins prepared by recombinant expression in a host cell as well as chemically synthesized nucleic acids.

The term "sample," is used in its broadest sense. A biological sample suspected of containing nucleic acids encoding at least one monoclonal antibody, or fragments thereof, or at least one monoclonal antibody itself and which sample can comprise a bodily fluid, an extract from a cell, chromosome, organelle, or membrane isolated from a cell, a cell, genomic DNA, RNA, or cDNA (in solution or bound to a solid support), a tissue, a tissue print, and the like.

As used herein any reference to "one aspect" or "an aspect" means that a particular element, feature, structure, or characteristic described in connection with the aspect is included in at least one aspect. The appearances of the phrase "in one aspect" in various places in the specification are not necessarily all referring to the same aspect.

The terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but can include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the aspects herein. This is done merely for convenience and to give a general sense of the invention. This description should be read to include one or at least one and the singular also includes the plural unless it is obvious that it is meant otherwise.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The present disclosure includes, but is not limited to, a method to derive monoclonal antibodies from an immunized organism. The organism can be an experimental organism treated with the antigen and appropriate adjuvant, or exposed to a pathogen or other biological agent. The organism can also be a human patient suffering from exposure to a pathogen or a disease. Since the method requires only small amounts of blood or tissue, the same organism can be sampled multiple times and subject to the following described analysis.

According to one aspect, the present disclosure provides methods for producing a monoclonal antibodies, the method comprising the steps of: (a) immunizing a host subject with an antigen; (b) creating a cDNA sequence library, the creating comprising the steps of: (i) isolating lymphocytes from the host subject, (ii) isolating mRNA from the lymphocytes, (iii) reverse transcribing the mRNA to cDNA, (iv) amplifying target antibody cDNA sequences, and (v) sequencing the target antibody cDNA sequences; and (c) analyzing the frequency of target antibody cDNA sequences, wherein target antibody cDNA sequences having a relatively high frequency are identified as candidate antibody sequences.

According to certain aspects, the lymphocytes comprise B cells and T cells. According to further aspects, the lymphocytes comprise isolated B cells.

In some aspects, methods are provided wherein the relative frequencies of target antibody cDNA sequences are compared before and after exposure to the antigen, wherein target antibody cDNA sequences having a significantly higher frequency after exposure to the antigen are identified as candidate antibody sequences.

In further aspects, a host subject is re-immunized with the antigen, a cDNA sequence library is created after the re-immunization, and the relative frequencies of the target antibody sequences are compared before and after the re-immunization, wherein antibody sequences present at a significantly higher frequency after the re-immunization are identified as mature candidate antibody sequences.

In some aspects, methods are provided wherein the relative frequencies of target antibody cDNA sequences are compared at two or more times after exposure to the antigen, wherein target antibody cDNA sequences having a significantly lower frequency in later times are identified as candidate antibody sequences.

Host Immunization and Antibody Production

Immunogens are delivered to a host for eliciting an immune response. The host can be any animal known in the art that is useful in biotechnological screening assays and is capable of producing recoverable antibodies when administered an immunogen, such as but not limited to, rabbits, mice, rats, hamsters, monkeys, baboons and humans. In yet another aspect, the host is transgenic and produces human antibodies, thereby greatly easing the development work for creating a human therapeutic.

In some aspects of the present disclosure, methods are provided wherein the target antibody sequences comprise immunoglobulin (Ig) heavy chain variable domain sequences. In further aspects the target antibody sequences comprise sequences of one or more complementarity determining regions (CDRs) of an immunoglobulin (Ig) heavy chain variable domain. In various aspects, a candidate antibody sequences with a light chain variable domain sequence and an Ig framework to produce a set of candidate monoclonal antibodies. In some aspects, the Ig framework is a human Ig framework.

In certain aspects, the host subject is an experimental animal. In some aspects, the host subject is a transgenic animal expressing human antibodies. In further aspects the host subject is a human patient that has been exposed to an antigen or a pathogen or is suffering from a disease which alters the adaptive immune response.

The term "antibody" refers to any immunoglobulin or intact molecule as well as to fragments thereof that bind to a specific epitope. Such antibodies include, but are not limited to polyclonal, monoclonal, chimeric, humanized, single chain, Fab, Fab', F(ab)' fragments and/or F(v) portions of the whole antibody. Antibodies can include monoclonal antibodies, polyclonal antibodies, single-chain antibodies, and fragments thereof which retain the antigen binding function of the parent antibody.

An intact "antibody" comprises at least two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, $CH_1$, $CH_2$ and $CH_3$. Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. The term antibody includes antigen-binding portions of an intact antibody that retain capacity to bind. Examples of binding include (i) a Fab fragment, a monovalent fragment consisting of the $V_L$, $V_H$, $C_L$ and CH1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the $V_L$ and $V_H$ domains of a single arm of an antibody, (v) a dAb fragment (Ward et al., Nature, 341:544-546 (1989)), which consists of a VH domain; and (vi) an isolated complementarity determining region (CDR).

The term "single chain antibodies" or "single chain Fv (scFv)" refers to an antibody fusion molecule of the two domains of the Fv fragment, $V_L$ and $V_H$. Although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al., Science, 242:423-426 (1988); and Huston et al., Proc Natl Acad Sci USA, 85:5879-5883 (1988)). Such single chain antibodies are included by reference to the term "antibody" fragments can be prepared by recombinant techniques or enzymatic or chemical cleavage of intact antibodies.

The term "antibody fragment" refers to an incomplete or isolated portion of the full sequence of the antibody which retains the antigen binding function of the parent antibody. Examples of antibody fragments include Fab, Fab', F(ab')2, and Fv fragments; diabodies; linear antibodies; single-chain antibody molecules; and multispecific antibodies formed from antibody fragments. Antibody fragments are encompassed by the present disclosure so long as they retain the desired affinity of the full-length antibody. In particular, it can be shorter by at least one amino acid.

Also, recombinant immunoglobulins can be produced. See, Cabilly, U.S. Pat. No. 4,816,567, incorporated herein by reference in its entirety and for all purposes; and Queen et al., Proc Natl Acad Sci USA, 86:10029-10033 (1989).

The term "monoclonal antibody" refers to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions (if present) derived from human germline immunoglobulin sequences.

The term "immune cell response" refers to the response of immune system cells to external or internal stimuli (e.g., antigen, cell surface receptors, cytokines, chemokines, and other cells) producing biochemical changes in the immune cells that result in immune cell migration, killing of target cells, phagocytosis, production of antibodies, other soluble effectors of the immune response, and the like.

"Immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, metastatic breast cancer cells, invading pathogens, cells or tissues infected with pathogens, or, in cases of autoimmunity or pathological inflammation, normal human cells or tissues.

The term "protective immunity" means that the subject mounts an active immune response to the immunogenic composition and/or that the subject has been provided with passive immunity, such that upon subsequent exposure or a challenge, the subject is able to resist and/or overcome infection and/or disease. Thus, a protective immune response will preferably decrease the incidence of morbidity and/or mortality from subsequent exposure to infection and/or disease.

"Adaptive immunity" or "adaptive immune response" are used interchangeably and in a broad sense herein and mean the immune response to antigen challenge, including the development of immunological memory. The adaptive immune response includes, without limitation, humoral and cellular immunity.

An "active immune response" is mounted by the host after exposure to immunogens by infection or by vaccination. In contrast, "passive immunity" is acquired through the transfer of preformed substances (e.g., antibodies, transfer factors, thymic grafts, interleukin-2, and the like) from an actively immunized host to a non-immune host.

"Lymphocyte" as used herein has the normal meaning in the art, and refers to any of the mononuclear, non-phagocytic leukocytes, found in the blood, lymph, and lymphoid tissues, e.g., B and T lymphocytes.

"T lymphocyte response" and "T lymphocyte activity" are used here interchangeably to refer to the component of immune response dependent on T lymphocytes (e.g., the proliferation and/or differentiation of T lymphocytes into helper, cytotoxic killer, or suppressor T lymphocytes, the provision of signals by helper T lymphocytes to B lymphocytes that cause or prevent antibody production, the killing of specific target cells by cytotoxic T lymphocytes, and the release of soluble factors such as cytokines that modulate the function of other immune cells).

Components of an immune response can be detected in vitro by various methods that are well known to those of ordinary skill in the art. For example, (1) cytotoxic T lymphocytes can be incubated with radioactively labeled target cells and the lysis of these target cells detected by the release of radioactivity; (2) helper T lymphocytes can be incubated with antigens and antigen presenting cells and the synthesis and secretion of cytokines measured by standard methods (Windhagen et al., Immunity, 2:373-380 (1995)); (3) antigen presenting cells can be incubated with whole protein antigen and the presentation of that antigen on MHC detected by either T lymphocyte activation assays or biophysical methods (Harding et al., Proc Natl Acad Sci, 86:4230-4234 (1989)); (4) mast cells can be incubated with reagents that cross-link their Fc-epsilon receptors and histamine release measured by enzyme immunoassay (Siraganian et al., TIPS, 4:432-437 (1983)).

Similarly, products of an immune response in either a model organism (e.g., mouse) or a human patient can also be detected by various methods that are well known to those of ordinary skill in the art. For example, (1) the production of antibodies in response to vaccination can be readily detected by standard methods currently used in clinical laboratories, e.g., an ELISA; (2) the migration of immune cells to sites of inflammation can be detected by scratching the surface of skin and placing a sterile container to capture the migrating cells over scratch site (Peters et al., Blood, 72:1310-1315 (1988)); (3) the proliferation of peripheral blood mononuclear cells in response to mitogens or mixed lymphocyte reaction can be measured using $^3$H-thymidine; (4) the phagocytic capacity of granulocytes, macrophages, and other phagocytes in peripheral blood mononuclear cells (PBMCs)s can be measured by placing PBMCs in wells together with labeled particles (Peters et al., Blood, 72:1310-1315 (1988)); and (5) the differentiation of immune system cells can be measured by labeling PBMCs with antibodies to CD molecules such as CD4 and CD8 and measuring the fraction of the PBMCs expressing these markers.

For convenience, immune responses are often described in the present disclosure as being either "primary" or "secondary" immune responses. A primary immune response, which is also described as a "protective" immune response, refers to an immune response produced in an individual as a result of some initial exposure (e.g., the initial "immunization") to a particular antigen, e.g., cell surface receptor, or activated integrin receptor. Such an immunization can occur, for example, as the result of some natural exposure to the antigen (for example, from initial infection by some pathogen that exhibits or presents the antigen) or from antigen presented by cancer cells of some tumor in the individual. Alternatively, the immunization can occur as a result of vaccinating the individual with a vaccine containing the antigen.

A primary immune response can become weakened or attenuated over time and can even disappear or at least become so attenuated that it cannot be detected. Accordingly, the present disclosure also relates to a "secondary" immune response, which is also described here as a "memory immune response." The term secondary immune response refers to an immune response elicited in an individual after a primary immune response has already been produced. Thus, a secondary or immune response can be elicited, e.g., to enhance an existing immune response that has become weakened or attenuated, or to recreate a previous immune response that has either disappeared or can no longer be detected. An agent that can be administrated to elicit a secondary immune response is after referred to as a "booster" since the agent can be said to "boost" the primary immune response.

As an example, and not by way of limitation, a secondary immune response can be elicited by re-introducing to the individual an antigen that elicited the primary immune response (for example, by re-administrating a vaccine). However, a secondary immune response to an antigen can also be elicited by administrating other agents that cannot contain the actual antigen. The secondary or memory immune response can be either a humoral (antibody) response or a cellular response. A secondary or memory humoral response occurs upon stimulation of memory B cells that were generated at the first presentation of the antigen. Delayed type hypersensitivity (DTH) reactions are a type of cellular secondary or memory immune response that are mediated by CD4+ cells. A first exposure to an antigen primes the immune system and additional exposure(s) results in a DTH.

According to certain aspects, the present disclosure provides that a host subject is immunized with multiple antigens. In further aspects, the monoclonal antibody is reactive to multiple antigens.

"Immunologically cross-reactive" or "immunologically reactive" refers to an antigen which is specifically reactive with an antibody which was generated using the same ("immunologically reactive") or different ("immunologically cross-reactive") antigen.

"Immunologically reactive conditions" refers to conditions which allow an antibody, generated to a particular epitope of an antigen, to bind to that epitope to a detectably greater degree than the antibody binds to substantially all other epitopes, generally at least two times above background binding, preferably at least five times above background. Immunologically reactive conditions are dependent upon the format of the antibody binding reaction and typically are those utilized in immunoassay protocols. See, Harlow and Lane, Antibodies, A Laboratory Manual (1988) for a description of immunoassay formats and conditions.

"Effector cell" refers to an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Effector cells express specific Fe receptors and carry out specific immune functions. An effector cell can induce antibody-dependent cell-mediated cytotoxicity (ADCC), e.g., a neutrophil capable of inducing ADCC. An effector cell can also phagocytose a target antigen, target cell, metastatic cancer cell, or microorganism.

The term "antigen" refers to a substance that prompts the generation of antibodies and can cause an immune response. It can be used interchangeably in the present disclosure with the term "immunogen". In the strict sense, immunogens are those substances that elicit a response from the immune system, whereas antigens are defined as substances that bind to specific antibodies. An antigen or fragment thereof can be a molecule (i.e., an epitope) that makes contact with a particular antibody. When a protein or a fragment of a protein is used to immunize a host animal, numerous regions of the protein can induce the production of antibodies (i.e., elicit the immune response), which bind specifically to the antigen (given regions or three-dimensional structures on the protein).

The term "epitope" refers to a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

Examples of the methods used for the production of the monoclonal antibodies of the present disclosure are given in EXAMPLES 1-5. These examples provide general methods used for the production of monoclonal antibodies.

In addition, techniques developed for the production of "chimeric antibodies" (Morrison et al., Proc Natl Acad Sci, 81:6851-6855 (1984)), incorporated herein by reference in their entirety) by splicing the genes from a mouse antibody molecule of appropriate antigen specificity together with genes from a human antibody molecule of appropriate biological activity can be used. For example, the genes from a mouse antibody molecule specific for an autoinducer can be spliced together with genes from a human antibody molecule of appropriate biological activity. A chimeric antibody is a molecule in which different portions are derived from different animal species, such as those having a variable region derived from a murine mAb and a human immunoglobulin constant region.

The term "human sequence antibody" includes antibodies having variable and constant regions (if present) derived from human germline immunoglobulin sequences. The human sequence antibodies of the present disclosure can include amino acid residues not encoded by human germline immunoglobulin sequences (e.g., mutations introduced by random or site-specific mutagenesis in vitro or by somatic mutation in vivo). Such antibodies can be generated in non-human transgenic animals, e.g., as described in PCT App. Pub. Nos. WO 01/14424 and WO 00/37504. However, the term "human sequence antibody", as used herein, is not intended to include antibodies in which CDR sequences derived from the germline of another mammalian species, such as a mouse, have been grafted onto human framework sequences (e.g., humanized antibodies).

The term "humanized antibody," refers to at least one antibody molecule in which the amino acid sequence in the non-antigen binding regions has been altered so that the antibody more closely resembles a human antibody, and still retains its original binding ability.

In addition, techniques have been developed for the production of humanized antibodies (see, e.g., U.S. Pat. Nos. 5,585,089 and 5,225,539, which are incorporated herein by reference in their entirety). An immunoglobulin light or heavy chain variable region consists of a "framework" region interrupted by three hypervariable regions, referred to as complementarity determining regions (CDRs). Briefly, humanized antibodies are antibody molecules from non-human species having one or more CDRs from the non-human species and a framework region from a human immunoglobulin molecule.

In certain aspects of the present disclosure, humanized antibodies are produced. In order to humanize an antibody derived from a different species, the antibody is sequenced and those sequences are placed into a human antibody backbone. Because certain sequences are predictably easier than others to place into the human backbone, the list of candidate sequences can be selected on the basis of ease of humanization.

In further aspects, the candidate sequences can be placed directly into a human backbone, thereby bypassing the steps of cloning and expression of the native non-humanized protein. Humanized animal technology is a method to create monoclonal antibodies that do not require humanization. The humanized antibodies are produced by creating a transgenic mouse wherein the native Ig loci are replaced with the corresponding human Ig loci. The resulting antibody is thus human and does not require humanization. However, this process still requires that a monoclonal antibody with a desired property is recovered from the humanized animal using either hybridoma or B cell isolation techniques.

Alternatively, techniques described for the production of single chain antibodies can be adapted to produce single chain antibodies against an immunogenic conjugate of the present disclosure. Single chain antibodies are formed by linking the heavy and light chain fragments of the Fv region via an amino acid bridge, resulting in a single chain polypeptide. Fab and F(ab')2 portions of antibody molecules can be prepared by the proteolytic reaction of papain and pepsin, respectively, on substantially intact antibody molecules by methods that are well-known. See e.g., U.S. Pat. No. 4,342,566. Fab' antibody molecule portions are also well-known and are produced from F(ab')2 portions followed by reduction of the disulfide bonds linking the two heavy chain portions as with mercaptoethanol, and followed by alkylation of the resulting protein mercaptan with a reagent such as iodoacetamide.

The antibodies of the present disclosure can bind to their corresponding antigen. For example, the antibodies can bind to a corresponding antigen displayed on the surface of a cell, in which case, the cell is targeted for immune mediated lysis. The monoclonal antibodies of the present disclosure have high affinity for their corresponding antigens.

According to some aspects, the present disclosure provides for a method for deriving monoclonal antibodies from an immunized organism. The organism can be an experimental organism treated with the antigen and appropriate adjuvant, or exposed to a pathogen or other biological agent. The organism can also be a human patient suffering from exposure to a pathogen or a disease. Since the method requires only small amounts of blood or tissue, the same organism can be sampled multiple times.

The antibody can be labeled with at least one radionuclide in order to improve targeting of infectious and/or diseased elements in vivo in at least a diagnostic and/or therapeutic capacity. The antibody can be labeled with at least one toxin and/or chemotherapeutic reagent. In particular, the labeled antibody can be used as an immunotoxin that better targets these toxic agents to infectious and/or diseased elements.

It will be appreciated that once the CDRs of an antibody are identified, conventional genetic engineering techniques can be used to devise expressible polynucleotides encoding any of the forms or fragments of antibodies described herein.

Adjuvants

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, chemokines, cofactors, toxins, plasmodia, synthetic compositions or LEEs or CEEs encoding such adjuvants.

Further suitable adjuvants can include, for example, any of the following: aluminum salts (alum), Complete Freund's adjuvant (CFA), Incomplete Freund's adjuvant (IFA), muramyl dipeptide (MDP). See, e.g., Ellouz et al., Biochem Biophys Res Commun, 59:1317 (1974). Synthetic analogs of MDP (see, Chedid et al., Prog Allergy, 25:63 (1978)), analogs of MDP including threonyl derivatives of MDP (Byars et al., Vaccine, 5:223 (1987)), n-butyl derivatives of MDP (Chedid et al., Infect Immun, 35:417), and a lipophilic derivative of a muramyl tripeptide (Gisler et al., in Immunomodulations of Microbial Products and Related Synthetic Compounds, 167 (1981)). MDP compounds, such as thur-MDP and nor-MDP, CGP (MTP-PE). Additional adjuvants include MF59 (See, e.g., Ott et al., "MF59—Design and Evaluation of a Safe and Potent Adjuvant for Human Vaccines" in Vaccine Design: The Subunit and Adjuvant Approach, 277-296 (1995)). QS21 is another adjuvant that has been shown to have significant immunological activity (Kensil et al., (1991); Wu et al., (1992); White et al., (1991) and White et al., Adv Exp Med Biol, 303:207-210 (1991)). Additional adjuvants include saponin (Kensil et al., J Immunol, 148:1519-1525 (1992); and Kensil et al., J Immunol, 146:431-437 (1991)). Yet further adjuvants according to the present methods include IL-1, IL-2, IL-4, IL-7, IL-12, γ-interferon, GMCSP, BCG, Resiquimod (R-848), aluminum hydroxide, lipid A, and monophosphoryl lipid A (MPL). RIBI, MPL, trehalose dimycolate (TDM) and cell wall skeleton (CWS) in a 2% squalene/Tween 80 emulsion is also contemplated.

Absence of Pre-Immunization

In another aspect, the present methods can be performed in the absence of pre-immunization data. For instance, this method is useful when pre-immune serum samples are not available such as can be the case if a human is exposed to a pathogen. Under these conditions, sequence frequency data post-infection is be used to derive a list of candidate antibody sequences as the number of circulating plasmacytes will fall off significantly. This technique is particularly useful for rapid antibody generation during epidemics.

Generation of Antibodies Against Multiple Related Antigens

In certain aspects of the present disclosure, different but related species of antigens are given to the host after multiple boosts. The antibodies are subsequently screened for cross-reactivity between multiple antigens, such as can be required for certain applications. For example, it can be desirable to create antibodies against a family of pathogen-derived proteins, or a set of synthetically designed proteins. In EXAMPLE 5 below, it is shown that multiple IgG heavy and variable domain sequences were present in both arm 3 and arm 5 of the experiment in high significance clusters. The presence of identical significant sequences across samples shows that there is a level of overlap between different animals in generating antibodies against a common antigen. Therefore, antibodies against shared epitopes can be found across multiple related antigens by immunizing related antigens into separate cohorts and comparing induced sequences between the cohorts. Accordingly, a single animal can be boosted with different, but related, antigens in order to determine whether there are sets of related sequences that are induced after each boost. Thus, one aspect of the present disclosure provides for antibodies having reactivity to greater than one antigen, especially where the antigens are related.

Negative Selection Antigens

In certain aspects of the present disclosure, a final boost of a background antigen, for which it is undesirable to have antibodies against, can be performed. In this case, MPSS data from post-immunization of the background antigen is used to screen out undesired antibody candidates. For example, a synthetic epitope or protein backbone might be used to assist in creation of the antigen, such that the same epitope or backbone could be placed in the background antigen. In this case, the candidate antibody sequences matching the background data set are removed from the list of antibody sequences.

According to certain aspects, the present disclosure provides methods for administering a background antigen and selecting against antibodies that are reactive to the background antigen. In further aspects, the background antigen is administered after a first antigen.

Isolation of Lymphocytes

Once the host has been immunized, lymphocytes can be isolated from circulating blood or other tissues as appropriate. Various methods for isolating lymphocytes are well known in the art, for example, lymphocytes can be isolated from human peripheral blood by standard density gradient centrifugation, apheresis, negative selection (e.g., by removing red blood cells using red blood cell-specific antibodies or by osmotic lysis of red blood cells followed by washing in PBS), or any other suitable means known in the art.

In some aspects, the B cells are isolated away from other blood lymphocytes by positive or negative selection techniques. Examples of reagents for isolating B-Cells include conjugated antibodies for positive selection such as anti-CD19 antibodies and pluralities of conjugated antibodies for negative selection such as anti-CD2, anti-CD3, anti-CD14, anti-CD16, anti-CD56, anti-Glycophorin A antibody cocktails, where the antibodies are conjugated to an appropriate support.

In another aspect, antigen specific B cells can be isolated, using a biotinylated form of the monomer linked to an immunomagnetic bead. In a further aspect, cell sorting is utilized to isolate desired B cells, such as B memory cells. One method of sorting which can be utilized in accordance with the present disclosure is a sorting method using magnetic beads, such as those produced by Dynal or Miltenyi, can be utilized. Another method of B cell selection that can be used is fluorescence-activated cell sorting (FACS). Since B memory cells have immunoglobulin on their surface, this specificity can be utilized to identify and capture these cells. Optionally, beads can be coated with an antigen of interest and attached to a column. B cells with immunoglobulin on their surface can be identified by FACS as well as by binding to the antigen. In certain aspects, B cells are selected by first biotinylating immunogens that bind to specific B cell receptors found on the surface of B cells specific to the monomer. Anti-biotin coated magnetic-activated cell sorting (MACs) beads can then be used to isolate bound B cells on magnetic columns.

Isolating mRNA

In the present disclosure, mRNAs derived from a small number of lymphocytes or B cells are used. mRNAs are extracted from isolated lymphocytes or isolated B cells. cDNAs are synthesized by using the extracted mRNAs as a template to obtain a cDNA library. Commercially available kits are conveniently used for extracting mRNAs and for constructing the cDNA library. Total cellular RNA can be isolated from a biological sample such as the isolated lymphocytes, or alternatively the isolated B cells, using any suitable technique such as the single-step guanidinium-thiocyanate-phenol-chloroform method described by Chomczynski and Sacchi (Anal Biochem, 162:156-159 (1987)). A portion of the total RNA comprises nucleic acid molecules encoding the heavy or entire light chain of antibodies produced in response to an immunogen.

In various aspects, the nucleic acid molecules are isolated from lymphocytes or B cells derived from an immunized subject. Methods of isolating mRNA encoding an antibody are well-known in the art. See, e.g., Sambrook et al. The mRNA can be used to produce cDNA for use in the polymerase chain reaction (PCR) or cDNA cloning of antibody genes. In another aspect, the nucleic acid is isolated from a non-human, non-transgenic animal. The nucleic acid molecules isolated from a non-human, non-transgenic animal can be used, e.g., for humanized antibodies.

Production and Amplification of cDNA

In certain aspects, mRNA in a biological sample is used to produce cDNA from a sample by reverse transcription using at least one primer; amplifying the cDNA so produced using polynucleotides as sense and antisense primers to amplify cDNAs therein; and detecting the presence of the amplified cDNA. In further aspects, the sequence of the amplified cDNA can be determined by any suitable method.

A number of methods for amplifying and/or detecting the presence of polynucleotides are well known in the art and can be employed in the practice of the present methods. For instance, reverse transcription-polymerase chain reaction (RT-PCR) can be used to amplify sequences encoding the conserved regions from RNA obtained from a variety of cell or tissue sources or cell lines. In practicing the invention, nucleic acids encoding the polypeptides of the invention, or modified nucleic acids, can be reproduced by, e.g., amplification. Amplification methods include, e.g., polymerase chain reaction, PCR (PCR PROTOCOLS, A GUIDE TO METHODS AND APPLICATIONS, ed. Innis, Academic Press, N.Y. (1990) and PCR STRATEGIES, ed. Innis, Academic Press, Inc., N.Y., ligase chain reaction (LCR) (1995) (see, e.g., Wu, Genomics, 4:560 (1989); Landegren, Science, 241:1077 (1988); Barringer, 89:117 (1990)); transcription amplification (see, e.g., Kwoh, Proc Natl Acad Sci USA, 86:1173 (1989)); and, self-sustained sequence replication (see, e.g., Guatelli, Proc Natl Acad Sci USA, 87:1874 (1990)); Q Beta replicase amplification (see, e.g., Smith, J Clin Microbiol, 35:1477-1491 (1997)), automated Q-beta replicase amplification assay (see, e.g., Burg, Mol Cell Probes, 10:257-271 (1996)) and other RNA polymerase mediated techniques (e.g., NASBA, Cangene, Mississauga, Ontario); see also Berger, Methods Enzymol, 152:307-316 (1987); Sambrook; Ausubel; U.S. Pat. Nos. 4,683,195 and 4,683,202; Sooknanan, Biotechnology, 13:563-564 (1995).

Methods for designing and using primers for RT-PCR are well known in the art and can be readily performed by one of skill in the art. Any number of appropriate sense and antisense probe combinations can be designed from a nucleotide sequence and used for this purpose.

In certain aspects, the B cells are isolated from other blood lymphocytes by positive or negative selection techniques before generating the mRNA sample. Additionally, a linear amplification step can be applied to create a more representative sequencing sample, for example T7 RNA polymerase sites can be placed in the cDNA primer in order to create more mRNA corresponding to the Ig heavy chain region by using T7 RNA polymerase, which can then be used for cDNA creation and PCR.

Sequencing

The methods of the present disclosure are not limited to any particular sequencing method but can be used in conjunction with essentially any sequencing methodology which relies on successive incorporation of nucleotides into a polynucleotide chain. Suitable techniques include, for example, Pyrosequencing™, FISSEQ (fluorescent in situ sequencing), MPSS (massively parallel signature sequencing), and sequencing by litigation-based methods, some of which are described in more detail below.

According to certain aspects, the present disclosure provides methods for sequencing the high affinity monoclonal antibodies. In further aspects, the relative frequencies of target antibody sequences are analyzed using a bioinformatics software algorithm. In yet further aspects the amplified target cDNA sequences are sequenced by massively parallel signature sequencing (MPSS).

In one aspect of the present disclosure, massively parallel methods are used for the identification and quantification of nucleotide sequences. Additionally, the method preferably exhibits a wide, dynamic range and high sensitivity enabling the quantitation of highly abundant as well as rare species. Also preferred is a method that provides an absolute measure of abundance, rather than relative quantitation as a ratio to a housekeeping or normalizing gene. Absolute abundance facilitates comparison of the nucleotide abundances between samples and between experiments, and allows the data from different runs to be "banked" in a database and directly compared. Finally, in order to permit the discovery of new nucleotide sequences, the method preferably provides direct sequence readout, and is independent of prior sequence knowledge. Several methods for nucleotide sequence analysis have been described that demonstrate one or more of these performance features.

The sequencing methods of Mermod et al. (PCT App. Pub. No. WO 00/18957) and Adessi et al., Nucleic Acids Res, 28(20):e87 (2000)) can also be used according to the present disclosure. They have described a method of solid-phase PCR in which highly multiplexed DNA colonies derived from individual DNA fragments are created on the surface of a solid support. In this method, primer pairs and templates containing universal priming sites are immobilized on the surface of a functionalized glass slide at a density appropriate for the generation of discrete colonies. Amplification of the templates occurs by primer extension in a process called "bridge amplification" to create on the order of two thousand copies of each template per colony. This method is purported to yield colonies at a density of millions of features per $mm^2$, which is suitable for genome-wide analysis. Sequence analysis of the colonies can be carried out by traditional methods, such as sequencing by addition or MPSS.

Leamon et al., have described a method of highly multiplexed genomic DNA amplification in a low volume plate-based platform that is also applicable to the present disclosure. PCR products derived from genomic fragments are attached to solid-phase beads, and sequencing of the fragments is carried out by synthesis using the Pyrosequencing™ technology. Such technology is applicable to the present disclosure.

Other appropriate sequencing methods include multiplex polony sequencing (as described in Shendure et al., Accurate Multiplex Polony Sequencing of an Evolved Bacterial Genome, Sciencexpress, Aug. 4, 2005, pg 1 available at www.sciencexpress.org/4 Aug. 2005/Page1/10.1126/science. 1117389, incorporated herein by reference), which employs immobilized microbeads, and sequencing in microfabricated picoliter reactors (as described in Margulies et al., Genome Sequencing in Microfabricated High-Density Picoliter Reactors, Nature, August 2005, available at www.nature.com/nature (published online 31 Jul. 2005, doi: 10.1038/nature03959, incorporated herein by reference). In certain aspects of the present disclosure, any one of these methods can be used to sequence the cDNA vectors to obtain sequence data on the isolated RNA sequences.

Massively Parallel Signature Sequencing (MPSS)

In certain aspects of the present disclosure, MPSS is used for sequencing cDNA. When using MPSS, a single species of DNA is attached to a solid support bead. Millions of these beads are created in a single reaction using emulsive PCR. The beads are placed in a chamber and subject to multiple rounds of pyrogenic sequencing, which is a chemistry that allows the beads to fluoresce depending on what base is next in the sequence. During each round the beads are photographed by a sensitive CCD camera and in this manner the sequence of the DNA on each of the bead is deduced. The result is that millions of sequences can be produced in a single run. Until recently, the length of these sequence reads were only 20 to 30 bases. Newer chemistry now allows for reads in the range of 400 bases, such as is the case with the Roche 454 titanium technology. These longer read methods allow of the generation of millions of 400 base long sequences in parallel which is a sufficient length to cover the entire variable domain region of both Ig heavy and light chain sequences. Furthermore, this type of sequencing does not require large amounts of starting material. For example, a long read MPSS run requires only 250 nanograms of DNA.

After hybridization, a minimum of one million beads are immobilized in a flow cell for sequencing biochemistry and imaging. The signature sequence on each bead is determined in parallel. The novel sequencing process involves repeatedly exposing four nucleotides by enzymatic digestion, ligating a family of encoded adapters, and decoding the sequence by sequential hybridization with fluorescent decoder probes.

The MPSS sequencing process is fully automated. Buffers and reagents are delivered to the beads in the flow cell via a proprietary instrumentation platform, and sequence-dependent fluorescent responses from the micro-beads are recorded by a CCD camera after each cycle.

MPSS data have many uses. The expression levels of nearly all polyadenylated transcripts can be quantitatively determined; the abundance of signatures is representative of the expression level of the gene in the analyzed tissue. Quantitative methods for the analysis of tag frequencies and detection of differences among libraries have been published and incorporated into public databases for SAGE™ data and are applicable to MPSS data. The availability of complete genome sequences permits the direct comparison of signatures to genomic sequences and further extends the utility of MPSS data. Because the targets for MPSS analysis are not pre-selected (like on a microarray), MPSS data are able to characterize the full complexity of transcriptomes, and can be used for "gene discovery". This is analogous to sequencing millions of ESTs at once, but the short length of the MPSS signatures makes the approach most useful in organisms for which genomic sequence data are available so that the source of the MPSS signature can be readily identified by computational means.

Additional information regarding MPSS technology can be obtained by reviewing the many publications on this subject, including U.S. Pat. Nos. 6,013,445, 5,846,719, and 5,714,330, all of which are incorporated herein by reference.

In one aspect of the present disclosure the heavy chain variable domain region for a specific isotype of antibody is used to create an MPSS library and subject to MPSS sequencing. The sample can be taken from lymphocytes or isolated B cells found in circulating blood or other appropriate tissue. In order to apply the MPSS sequencing technology, specific DNA sequence tags must be placed at either end of the region of DNAs to be sequenced. This can be accomplished by creating a cDNA from mRNA taken from B cells using reverse-transcriptase, and then applying polymerase chain reaction (PCR) using primers with both the appropriate isotype specific sequences and the MPSS tags to generate the DNA library.

The MPSS method involves significant amounts of digital analysis. As a result, perfect sequence subtraction and analysis can be preformed, as opposed to physical methods which are always subject to imperfections and contamination. Also, unlike physical methods, the digital analysis technique can be altered and applied multiple times without the need for additional physical samples.

More precise information about the candidate antibody sequences can be produced by more frequent sampling using MPSS. Samples might be taken as the organism's response falls back to background levels and to establish the background before the next boost. Another advantage of multiple data points is that affinity maturation data of the antibody can be generated. For example one or more highly related antibodies to an antibody detected in a previous sample might appear over time that represents a B cell line which has undergone affinity maturation. Affinity matured antibodies have higher affinity for the target sequence than the parental sequence, so identification of these sequences can be desirable.

In certain aspects, the list of candidate sequences might be changed by applying filters based on the DNA sequence or predicted protein sequence. For example, if additional cysteine residues are present in the sequence, which are judged as likely to create potential difficulties in manufacturing of the protein, those sequences could be removed from the candidate antibody sequence list. Other properties of the predicted protein sequences could also be used, such as the presence or absence of charged residues, or conformance to canonical antibody sequence patterns.

Nucleic Acids

According to another aspect, the present disclosure provides an isolated nucleic acid molecule encoding: at least one heavy chain of an antibody or a fragment thereof as identified by the present methods and/or at least one light chain of an antibody as identified by the present methods. In further aspects, the present disclosure provides for variants, mutants or fragments of the isolated nucleic acids as well.

According to further aspects, the present disclosure provides an expression vector comprising the nucleic acid which encodes an antibody identified according to the present methods and a host cell comprising the expression vector. In particular, the vectors can comprise, but are not limited to, lentiviral vectors, retroviral vectors, adenoviral vectors, adeno-associated virus vectors and Herpes Simplex Virus vectors. More in particular, retroviral vectors can be used for delivery of the constructs either in vitro, ex vivo or in vivo.

Recombinant Nucleic Acid Techniques

The nucleic acids used to practice this invention, whether RNA, siRNA, antisense nucleic acid, cDNA, genomic DNA, vectors, viruses or hybrids thereof, can be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, e.g., Adams, J Am Chem Soc, 105:661 (1983); Belousov, Nucleic Acids Res, 25:3440-3444 (1997); Frenkel, Free Radic Biol Med, 19:373-380 (1995); Blommers, Biochemistry, 33:7886-7896 (1994); Narang, Meth Enzymol, 68:90 (1979); Brown, Meth Enzymol, 68:109 (1979); Beaucage, Tetra Lett, 22:1859 (1981); U.S. Pat. No. 4,458,066.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook and Russell, ed., MOLECULAR CLONING: A LABORATORY MANUAL (3rd ED.), Vols. 1-3, Cold Spring Harbor Laboratory (2001); CURRENT PROTOCOLS 1N MOLECULAR BIOLOGY; Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g., fluid or gel precipitin reactions, immunodiffusion, immuno-electrophoresis, radioimmunoassay (RIAs), enzyme-linked immunosorbent assays (ELISAs), immuno-fluorescent assays, Southern analysis, Northern analysis, dot-blot analysis, gel electrophoresis (e.g., SDS-PAGE), nucleic acid or target or signal amplification methods, radiolabeling, scintillation counting, and affinity chromatography.

Obtaining and manipulating nucleic acids used to practice the methods of the present disclosure can be done by cloning from genomic samples, and, if desired, screening and re-cloning inserts isolated or amplified from, e.g., genomic clones or cDNA clones. Sources of nucleic acid used in the methods of the present disclosure include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld, Nat Genet, 15:333-335 (1997); yeast artificial chromosomes (YAC); bacterial artificial chromosomes (BAC); P1 artificial chromosomes, see, e.g., Woon, Genomics, 50:306-316 (1998); P1-derived vectors (PACs), see, e.g., Kern, Biotechniques, 23:120-124 (1997); cosmids, recombinant viruses, phages or plasmids.

The present disclosure provides fusion proteins and nucleic acids encoding an antibody as identified by the present methods. An antibody can be fused to a heterologous peptide or polypeptide, such as N-terminal identification peptides which impart desired characteristics, such as increased stability or simplified purification. Peptides and polypeptides of the present disclosure can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Sigma Aldrich, St. Louis, Mo.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams, Biochemistry, 34:1787-1797 (1995); Dobeli, Protein Expr Purif, 12:404-414 (1998). The histidine residues facilitate detection and purification while the enterokinase cleavage site provides a means for purifying the epitope from the remainder of the fusion protein. In one aspect, a nucleic acid encoding a polypeptide is assembled in appropriate phase with a leader sequence capable of directing secretion of the translated polypeptide or fragment thereof. Technology pertaining to vectors encoding fusion proteins and application of fusion proteins are well described in the scientific and patent literature, see e.g., Kroll, DNA Cell Biol, 12:441-53 (1993).

In some aspects, a nucleic acid encoding a heavy chain of an antibody of the present disclosure can comprise a nucleotide sequence encoding a $V_H$ domain of the present disclosure joined in-frame to a nucleotide sequence encoding a heavy chain constant domain from any source. Similarly, a nucleic acid molecule encoding a light chain of an antibody as identified by the present methods can comprise a nucleotide sequence encoding a $V_L$ domain of the present disclosure joined in-frame to a nucleotide sequence encoding a light chain constant domain from any source.

In a further aspect of the present disclosure, nucleic acid molecules encoding the variable domain of the heavy ($V_H$) and light ($V_L$) chains are "converted" to full-length antibody genes. In one aspect, nucleic acid molecules encoding the $V_H$ or $V_L$ domains are converted to full-length antibody genes by insertion into an expression vector already encoding heavy chain constant ($C_H$) or light chain ($C_H$) constant domains, respectively, such that the $V_H$ segment is operatively linked to the $C_H$ segment(s) within the vector, and the $V_L$ segment is operatively linked to the $C_L$ segment within the vector. In another aspect, nucleic acid molecules encoding the $V_H$ and/or $V_L$ domains are converted into full-length antibody genes by linking, e.g., ligating, a nucleic acid molecule encoding a $V_H$ and/or $V_L$ domains to a nucleic acid molecule encoding a $C_H$ and/or $C_L$ domain using standard molecular biological techniques. Nucleic acid sequences of human heavy and light chain immunoglobulin constant domain genes are known in the art. See, e.g., Kabat et al., Sequences of Proteins of Immunological Interest, 5th Ed., NIH Publ. No. 91-3242 (1991). Nucleic acid molecules encoding the full-length heavy and/or light chains can then be expressed from a cell into which they have been introduced and the particular monoclonal antibody isolated.

The nucleic acid molecules can be used to recombinantly express large quantities of monoclonal antibodies. The nucleic acid molecules also can be used to produce chimeric antibodies, bispecific antibodies, single chain antibodies, immunoadhesins, diabodies, mutated antibodies and antibody derivatives, as described further below. If the nucleic acid molecules are derived from a non-human, non-transgenic animal, the nucleic acid molecules can be used for antibody humanization, also as described herein.

In another aspect, a nucleic acid molecule of the present disclosure is used as a probe or PCR primer for a specific antibody sequence. For instance, the nucleic acid can be used as a probe in diagnostic methods or as a PCR primer to amplify regions of DNA that could be used, inter alia, to isolate additional nucleic acid molecules encoding variable domains of particular antibodies. In some aspects, the nucleic acid molecules are oligonucleotides. In some aspects, the oligonucleotides are from highly variable regions of the heavy and light chains of the antibody of interest.

Transcriptional Control Elements

The nucleic acids, as aspects of the present disclosure, can be operatively linked to a promoter. A promoter can be one motif or an array of nucleic acid control sequences which direct transcription of a nucleic acid. A promoter can include necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter which is active under most environmental and developmental conditions. An "inducible" promoter is a promoter which is under environmental or developmental regulation. A "tissue specific" promoter is active in certain tissue types of an organism, but not in other tissue types from the same organism. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

Expression Vectors and Cloning Vehicles

Aspects of the present disclosure provide expression vectors and cloning vehicles comprising nucleic acids of the invention, e.g., sequences encoding the proteins of the invention. Expression vectors and cloning vehicles can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, Aspergillus* and yeast). Vectors can include chromosomal, non-chromosomal and synthetic DNA sequences. Large numbers of suitable vectors are known to those of skill in the art, and are commercially available.

The nucleic acids of the present disclosure can be cloned, if desired, into any of a variety of vectors using routine molecular biological methods; methods for cloning in vitro amplified nucleic acids are described, e.g., U.S. Pat. No. 5,426,039. To facilitate cloning of amplified sequences, restriction enzyme sites can be "built into" a PCR primer pair.

The present disclosure provides libraries of expression vectors encoding polypeptides and peptides of the invention. These nucleic acids can be introduced into a genome or into the cytoplasm or a nucleus of a cell and expressed by a variety of conventional techniques, well described in the scientific and patent literature. See, e.g., Roberts, Nature, 328:731 (1987); Schneider, Protein Expr Purif, 6435:10 (1995); Sambrook, Tijssen or Ausubel. The vectors can be isolated from natural sources, obtained from such sources as ATCC or GenBank libraries, or prepared by synthetic or recombinant methods. For example, the nucleic acids of the present disclosure can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required.

In one aspect, the nucleic acids of the present disclosure are administered in vivo for in situ expression of the peptides or polypeptides of the present disclosure. The nucleic acids can be administered as "naked DNA" (see, e.g., U.S. Pat. No. 5,580,859) or in the form of an expression vector, e.g., a recombinant virus. The nucleic acids can be administered by any route, including peri- or intra-tumorally, as described below. Vectors administered in vivo can be derived from viral genomes, including recombinantly modified enveloped or non-enveloped DNA and RNA viruses, preferably selected from baculoviridiae, parvoviridiae, picornoviridiae, herpesveridiae, poxyiridae, adenoviridiae, or picornnaviridiae. Chimeric vectors can also be employed which exploit advantageous merits of each of the parent vector properties (See e.g., Feng, Nature Biotechnology, 15:866-870 (1997)). Such viral genomes can be modified by recombinant DNA techniques to include the nucleic acids of the present disclosure; and can be further engineered to be replication deficient, conditionally replicating or replication competent. In alternative aspects, vectors are derived from the adenoviral (e.g., replication incompetent vectors derived from the human adenovirus genome, see, e.g., U.S. Pat. Nos. 6,096,718; 6,110,458; 6,113,913; 5,631,236); adeno-associated viral and retroviral genomes. Retroviral vectors can include those based upon murine leukemia virus (MuLV), gibbon ape leukemia virus (GaLV), Simian Immuno deficiency virus (SIV), human immuno deficiency virus (HIV), and combinations thereof; see, e.g., U.S. Pat. Nos. 6,117,681; 6,107,478; 5,658,775; 5,449,614; Buchscher, J Virol, 66:2731-2739 (1992); Johann, J Virol, 66:1635-1640 (1992). Adeno-associated virus (AAV)-based vectors can be used to adioimmun cells with target nucleic acids, e.g., in the in vitro production of nucleic acids and peptides, and in in vivo and ex vivo gene therapy procedures; see, e.g., U.S. Pat. Nos. 6,110,456; 5,474,935; Okada, Gene Ther, 3:957-964 (1996).

The term "expression cassette" refers to a nucleotide sequence which is capable of affecting expression of a structural gene (i.e., a protein coding sequence, such as a polypeptide of the present disclosure) in a host compatible with such sequences. Expression cassettes include at least a promoter operably linked with the polypeptide coding sequence; and, optionally, with other sequences, e.g., transcription termination signals. Additional factors necessary or helpful in effecting expression can also be used, e.g., enhancers.

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination. Thus, expression cassettes also include plasmids, expression vectors, recombinant viruses, any form of recombinant "naked DNA" vector, and the like.

The term "vector" is intended to refer to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" can be used interchangeably as the plasmid is the most commonly used form of vector. However, the present disclosure is intended to include such other forms of expression vectors, such as viral vectors (e.g., replication defective retroviruses, adenoviruses and adeno-associated viruses), which serve equivalent functions.

Host Cells and Transformed Cells

The present disclosure also provides a transformed cell comprising a nucleic acid sequence of the invention, e.g., a sequence encoding a polypeptide of the invention, or a vector of the invention. The host cell can be any of the host cells familiar to those skilled in the art, including prokaryotic cells, eukaryotic cells, such as bacterial cells, fungal cells, yeast cells, mammalian cells, insect cells, or plant cells. Exemplary bacterial cells include *E. coli, Streptomyces, Bacillus subtilis, Salmonella typhimurium* and various species within the genera *Pseudomonas, Streptomyces,* and *Staphylococcus*. Exemplary insect cells include *Drosophila* S2 and *Spodoptera* Sf9. Exemplary animal cells include CHO, COS or Bowes melanoma or any mouse or human cell line. The selection of an appropriate host is within the abilities of those skilled in the art.

The vector can be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation.

Engineered host cells can be cultured in conventional nutrient media modified as appropriate for activating promoters, selecting transformants or amplifying the genes of the present disclosure. Following transformation of a suitable host strain and growth of the host strain to an appropriate cell density, the selected promoter can be induced by appropriate means (e.g., temperature shift or chemical induction) and the cells can be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector can be glycosylated or can be non-glycosylated. Polypeptides of the present disclosure can or can not also include an initial methionine amino acid residue.

Cell-free translation systems can also be employed to produce a polypeptide of the present disclosure. Cell-free translation systems can use mRNAs transcribed from a DNA construct comprising a promoter operably linked to a nucleic acid encoding the polypeptide or fragment thereof. In some aspects, the DNA construct can be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

Functional Moieties

In one aspect, the monoclonal antibodies generated according to the present methods can be modified to have at least one functional moiety, such as but not limited to, a detectable moiety or a therapeutic moiety, bound thereto. For example, but not by way of limitation, the detectable moiety can be selected from the group consisting of a fluorophore, an enzyme, a radioisotope and combinations thereof, while the therapeutic moiety can be selected from the group consisting of a cytotoxic moiety, a toxic moiety, a cytokine moiety, a bi-specific antibody moiety, and combinations thereof.

Many methods are known in the art to conjugate or fuse (couple) molecules of different types, including peptides. These methods can be used according to the present disclosure to couple an antibody another moiety, such as a therapeutic moiety or an identifiable moiety, to thereby provide an immunotoxin or immunolabel.

Two isolated peptides can be conjugated or fused using any conjugation method known to one skilled in the art. A peptide can be conjugated to an antibody of interest, using a 3-(2-pyridyldithio)propionic acid N-hydroxysuccinimide ester (also called N-succinimidyl 3-(2-pyridyldithio) propionate) ("SDPD"), a glutaraldehyde conjugation procedure, or a carbodiimide conjugation procedure.

Any SPDP conjugation method known to those skilled in the art can be used. For example, in one illustrative aspect, the method of conjugation by Cumber et al., Methods of Enzymology, 112:207-224 (1985), can be used.

Conjugation of a peptide (e.g., an identifiable or therapeutic moiety) with an antibody can be accomplished by methods known to those skilled in the art using glutaraldehyde. For example, in one illustrative aspect, the method of conjugation by G. T. Hermanson, "Antibody Modification and Conjugation, in Bioconjugate Techniques", Academic Press, San Diego (1996) can be used.

Conjugation of a peptide with an antibody can be accomplished by methods known to those skilled in the art using a dehydrating agent such as a carbodiimide. Most preferably the carbodiimide is used in the presence of 4-dimethyl aminopyridine. As is well known to those skilled in the art, carbodiimide conjugation can be used to form a covalent bond between a carboxyl group of peptide and an hydroxyl group of an antibody (resulting in the formation of an ester bond), or an amino group of an antibody (resulting in the formation of an amide bond) or a sulfhydryl group of an antibody (resulting in the formation of a thioester bond).

Likewise, carbodiimide coupling can be used to form analogous covalent bonds between a carbon group of an antibody and a hydroxyl, amino or sulfhydryl group of the peptide. See, generally, March, Advanced Organic Chemistry: Reaction's, Mechanism, and Structure, 3d ed.: 349-50 & 372-74 (1985). By means of illustration, and not limitation, the peptide is conjugated to an antibody via a covalent bond using a carbodiimide, such as dicyclohexylcarbodiimide. See generally, the methods of conjugation by Neises et al., Angew Chem, Int Ed Engl, 17:522 (1978); Hassner et al., Tetrahedron Lett, 4475 (1978); Boden et al., J Org Chem, 50:2394 (1986) and Mathias, Synthesis, 561 (1979).

Antibody Assays

According to certain aspects, the present disclosure provides methods for assaying the candidate monoclonal antibodies for affinity to an antigen. In further aspects, the present disclosure provides for subjecting the candidate monoclonal antibodies to positive selection to identify high affinity monoclonal antibodies. In yet further aspects, subjecting the candidate monoclonal antibodies to positive selection comprises contacting the candidate monoclonal antibodies to the antigen bound to a substrate and isolating bound antibodies from unbound antibodies.

The terms "specific binding" or "specifically binding" refer to the interaction between the antigen and their corresponding antibodies. The interaction is dependent upon the presence of a particular structure of the protein recognized by the binding molecule (i.e., the antigen or epitope). In order for binding to be specific, it should involve antibody binding of the epitope(s) of interest and not background antigens.

Once the antibodies are produced, they are assayed to confirm that they are specific for the antigen of interest and to determine whether they exhibit any cross reactivity with other antigens. One method of conducting such assays is a sera screen assay as described in U.S. App. Pub. No. 2004/0126829, the contents of which are hereby expressly incorporated herein by reference. However, other methods of assaying for quality control are within the skill of a person of ordinary skill in the art and therefore are also within the scope of the present disclosure.

Antibodies, or antigen-binding fragments, variants or derivatives thereof of the present disclosure can also be described or specified in terms of their binding affinity to an antigen. The affinity of an antibody for an antigen can be determined experimentally using any suitable method. (See, e.g., Berzofsky et al., "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer.

The affinity binding constant ($K_{aff}$) can be determined using the following formula:

$$K_{aff} = \frac{(n-1)}{2(n[mAb']_t - [mAb]_t)}$$

in which:

$$n = \frac{[mAg]_t}{[mAg']_t}$$

[mAb] is the concentration of free antigen sites, and [mAg] is the concentration of free monoclonal binding sites as determined at two different antigen concentrations (i.e., $[mAg]_t$ and $[mAg']_t$) (Beatty et al., J Imm Meth, 100:173-179 (1987)).

The term "high affinity" for an antibody refers to an equilibrium association constant ($K_{aff}$) of at least about $1\times10^7$ liters/mole, or at least about $1\times10^8$ liters/mole, or at least about $1\times10^9$ liters/mole, or at least about $1\times10^{10}$ liters/mole, or at least about $1\times10^{11}$ liters/mole, or at least about $1\times10^{12}$ liters/mole, or at least about $1\times10^{13}$ liters/mole, or at least about $1\times10^{14}$ liters/mole or greater. "High affinity" binding can vary for antibody isotypes.

EXEMPLARY ASPECTS

Example 1

Antigen Specific Ig Heavy Chain Variable Region Candidate Library Generation

FIG. 1 describes a representative process of identification of antigen-specific heavy chain sequences using MPSS and bioinformatic subtraction. In this example, an isotype of Ig heavy chain's variable region is used to create a sample for MPSS sequencing as described above. Samples are generated from the organism both before and after exposure to the antigen. Once these data are generated, then the sequences are compared using a bioinformatic algorithm which identifies those sequences which are significantly amplified or appear only after exposure to the antigen. Those sequences matching these criteria are used to create a set of candidate antigen specific heavy chain sequences. Due to the large number of sequences generated by MPSS, it is possible to estimate the relative abundance of individual sequences by counting the number of times that sequences appears in the database. This quantitative estimate can be used to find sequences that are present in significantly greater numbers in the post-immunized sample as compared to the pre-immunized sample.

Example 2

Figure 2:
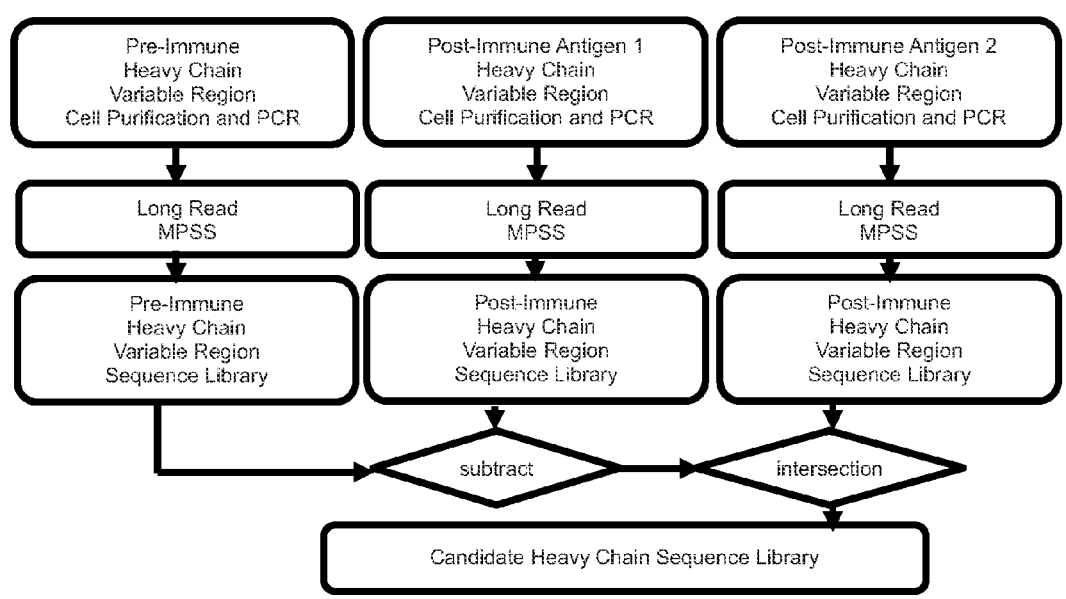
FIG. 2: Heavy Chain Sequence Library Generation using Multiple Boosts/Antigens. This figure is an extension of FIG. 1 whereby the variable region is sampled at multiple times after repeated boost with the same or related antigens. These data are digitally analyzed in order to identify candidate antibody variable domains that are induced after each boost which will react with the antigen(s).

Antigen Specific Ig Heavy Chain Variable Region Candidate Library Generation from Multiple Boosts or Antigens FIG. 2 describes an extension of the method described in FIG. 1 which can be used to identify antibodies that react to multiple related antigens or reaction to a single antigen over multiple boosts. In this example, Ig heavy chain specific MPSS sequencing is applied to the organism after each immunization with the same or different antigens and the bioinformatic subtraction is performed using the pre-immune sequences, while the intersection or union of the remaining sequences is performed between the first post-immune sample and the second post-immune sample. Stated otherwise, sequences common to the post-immune samples but not present, or present in significantly lower levels in the pre-immune sample are selected. One variant of this method is to look for related but not identical heavy chain regions that might represent affinity maturation of the antibody induced by multiple exposures to the same or related antigens.

Example 3

Formula for Variable Region Homology Tree Probability Calculation

Given a set of samples taken from different experimental arms at different time points and/or tissues, those samples can be divided into a foreground set A, a background set B, or neither, depending on the circumstances of the experiment and the calculation to be performed. The chances of a random occurrence of m of sequences or more in set A, compared to the total number of sequences n in both foreground A and background B sets defines the e-score, E(m,m,Pa), and is calculated using the following formula:

$$Pa = \frac{(\text{number of samples in set } A)}{(\text{number of samples in set } A)(\text{number of sample in set } B)}$$

wherein Pa is defined as the probability of a sequence being in set A.

The binomial coefficient, i.e., the number of ways in which k items can be chosen from a set of n choices, can be determined using the following formula:

$$C(k, n) = \frac{n!}{k!(n-k)!}$$

wherein the symbol "!" indicates the integer factorial function.

The probability of k occurrences in set A is given by the following formula:

$$C(k,n)(Pa^k)((1-Pa)^{(n-k)})$$

The probability of m or more occurrences of sequences in set A is determined from the sum from m to n in the following formula:

$$E(n, m, Pa) = \sum_{K=m}^{n} C(k, n)(Pa^k)((1 - Pa)^{(n-k)})$$

The value E(m,m,Pa) is a calculation of the e-score, which is defined to be the chance at random of the event occurring n or more times in Pa versus anything other than Pa; i.e., the likelihood of m or more occurrences in set A out of n total events.

When this formula is applied to NGS sequence data potential errors from both sequencing and from sample preparation must be taken into account. While it can be applied at the individual sequence level the numerical count for that sequence may not be great enough for statistical significance. The e-score formula can also be applied to clusters of related sets of sequences and thus have higher significance values and be more tolerant of possible errors in the data. The logic is as follows: since not only is this single sequence present mostly in the set A and not set B, and all the most closely related sequences are also over-represented in set A but not set B, then the single sequence is more likely to be genuinely present in the sample than if the related sequences were not present.

In order to apply the formula to clusters of sequences, a phylogenetic tree can be created from the NGS sequence data. First a similarity score must be generated against each other member for the sequences between the primer sites. These scores are used to populate a similarity matrix. This matrix can be populated by using, as an example, the blast score resulting from an all-against-all blast searching. Next these data are used to produce clusters of sequences.

Figure 3A:
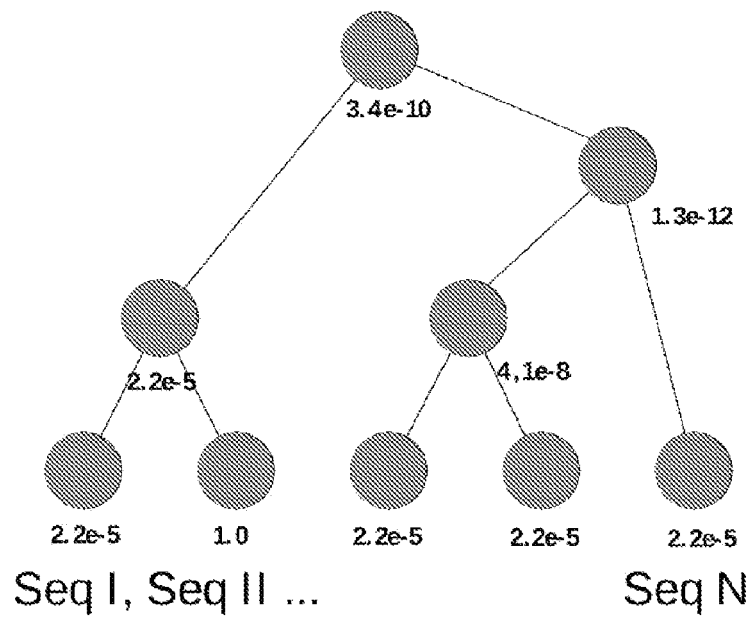
FIG. 3: Cluster based e-score analysis. (A) This figure shows the process of identifying peak nodes of statistical significance starting from barcoded NGS sequence data. (B) This figure shows histograms of the negative log of e-scores from the indicated experimental arm peak nodes on the upper Y axis, and the log inverse control scores in the lower Y axis. Experimental scores for experimental cohorts are indicated arm 1 . . . 5 and the inverse scores are indicated rev 1 . . . 5. The four graphs show the effects of different values of T from 1 to 1000 on the e-scores.
Figure 3A:
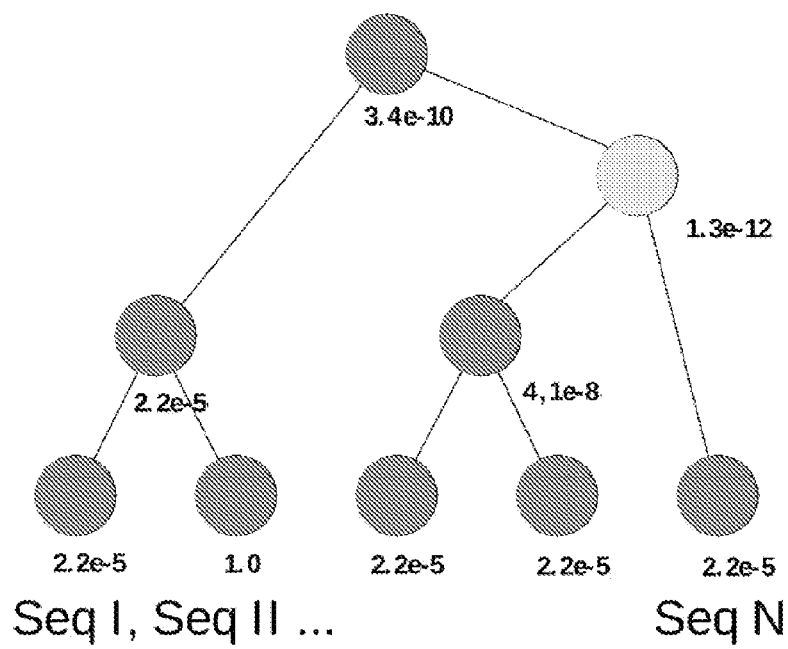
Figures 1, 3B:
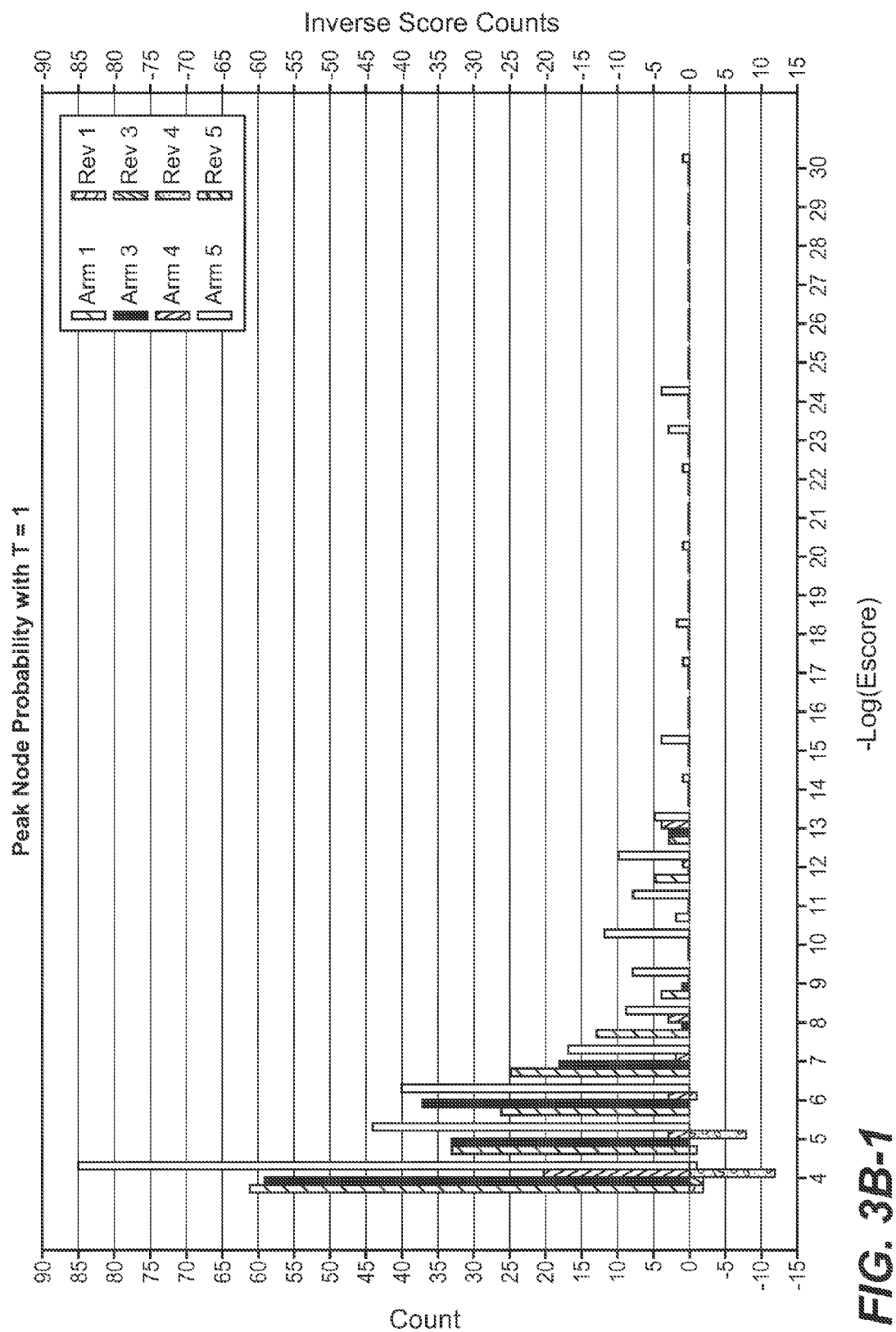
Figures 2, 3B:
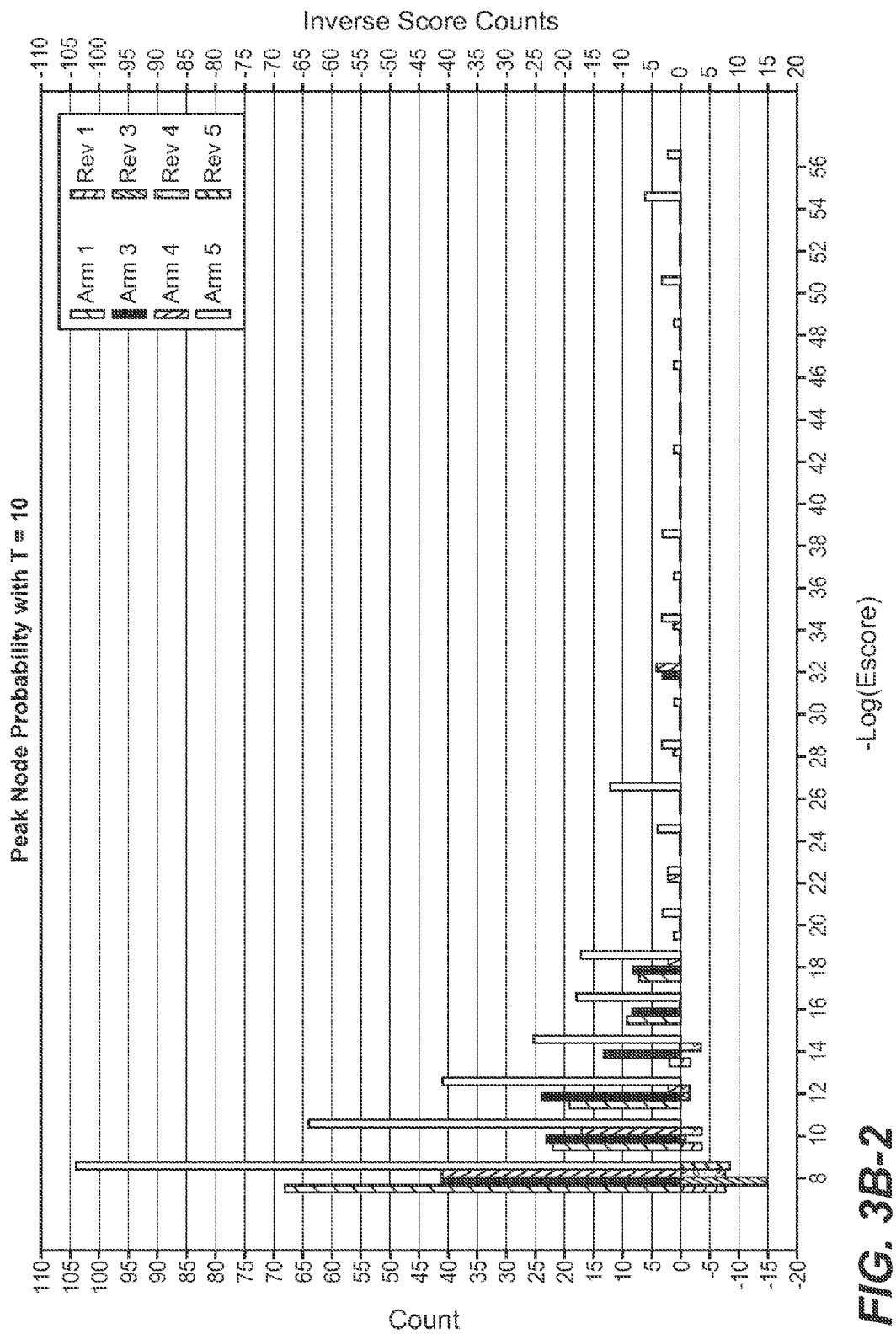
Figures 3, 3B:
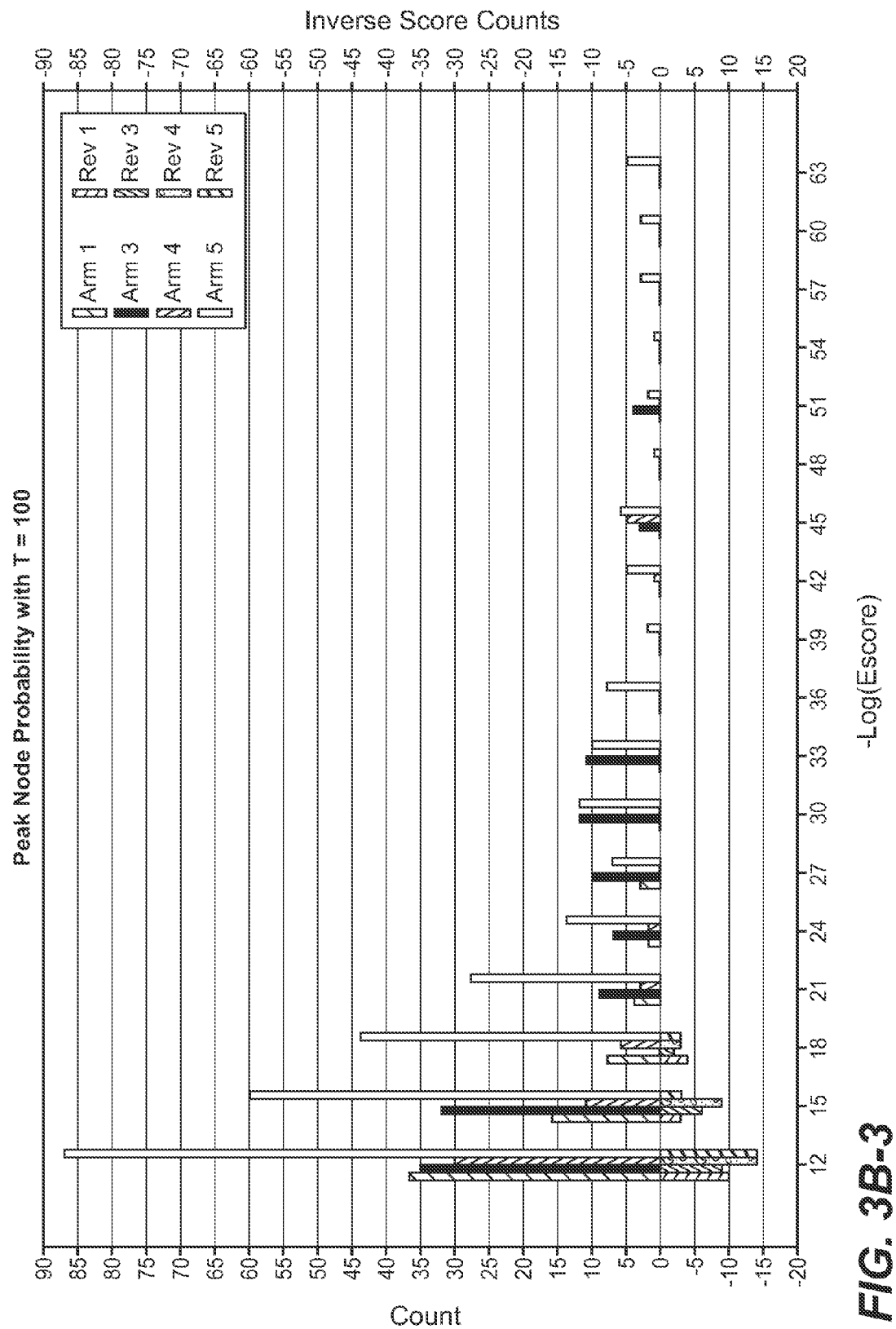

FIG. 3 summarizes the process of using NGS sequence data in creating the phylogenetic tree and assigning significance values to the leaf and node elements of the tree.

From the matrix data, a phylogenetic tree can be constructed using an aggolmerative clustering algorithm such as Unweighted Pair Group Method with Arithmetic mean, (UPGMA). The expected formula E(m, m, Pa) can be applied to each node of the resulting tree, where the total events in the foreground or background are the sum of foreground or background events in the child nodes. This provides a straightforward statistical significance measure to sets of related sequences, rather than sequences measured one-by-one.

In order to divide the tree into significance-based subsets, peak nodes of e-scores in a given tree can be selected. A peak node is a node of the tree whose parent and child node's e-scores are less significant than its own. These represent local maximums in the tree graph, and the counts and significance of these nodes can be used to report overall differences between foreground and background sample sets.

How the raw count of a given sequence in a sample relates to the expected score formula depends on whether or not the events are independent. For example, if amplification of a sample by means such as non-linear PCR has the potential to favor one sequence over others, then counts of those sequences in a given sample would not be completely independent. If the events are totally dependent then one event would count the same as 100 events in a given PCR sample. On the other extreme, if the sequences are totally independent then each occurrence counts equally, whether one or 100 are detected in a sample. A generalization of the e-score formula is to limit the total counts allowed from a sample to a maximum number T. For example T=100 means that occurrences of sequences more than 100 times in a sample are not considered independent events, but less than 20 are. This parameter is T. FIG. 3B shows the effects of different values of T on significance scores of the 5 test arms described in the experimental method tested against naive controls. As an additional control for the calculation, the e-score of the background set against the foreground set can be calculated. In other words, by swapping the foreground with the background, the probability of sequence clusters being significant in the naive set as compared to the experiment set can be calculated. Graphed in the lower half of the graph are the scores for the corresponding inverse experiment which measures the probability of sequences from the naive arm being unique relative to the test arm. The presence of fewer of these scores and their lower significance indicate that most unique sets of sequences are present in the experimental sample set rather than the naive set. The presence of most of the very high probability specific sequences in experimental arms 3 and 5 correlates with the strongest immune response seen in those arms as measured by antigen blocking activity in the serum. This indicates that most of the sequences farther down the tree are produced in response to treatment as compared to the control samples. The likelihood of a given sequence in the set of being antigen-specific is extremely high.

Example 4

Light Chain Matching

Figures 3, 3B, 4:
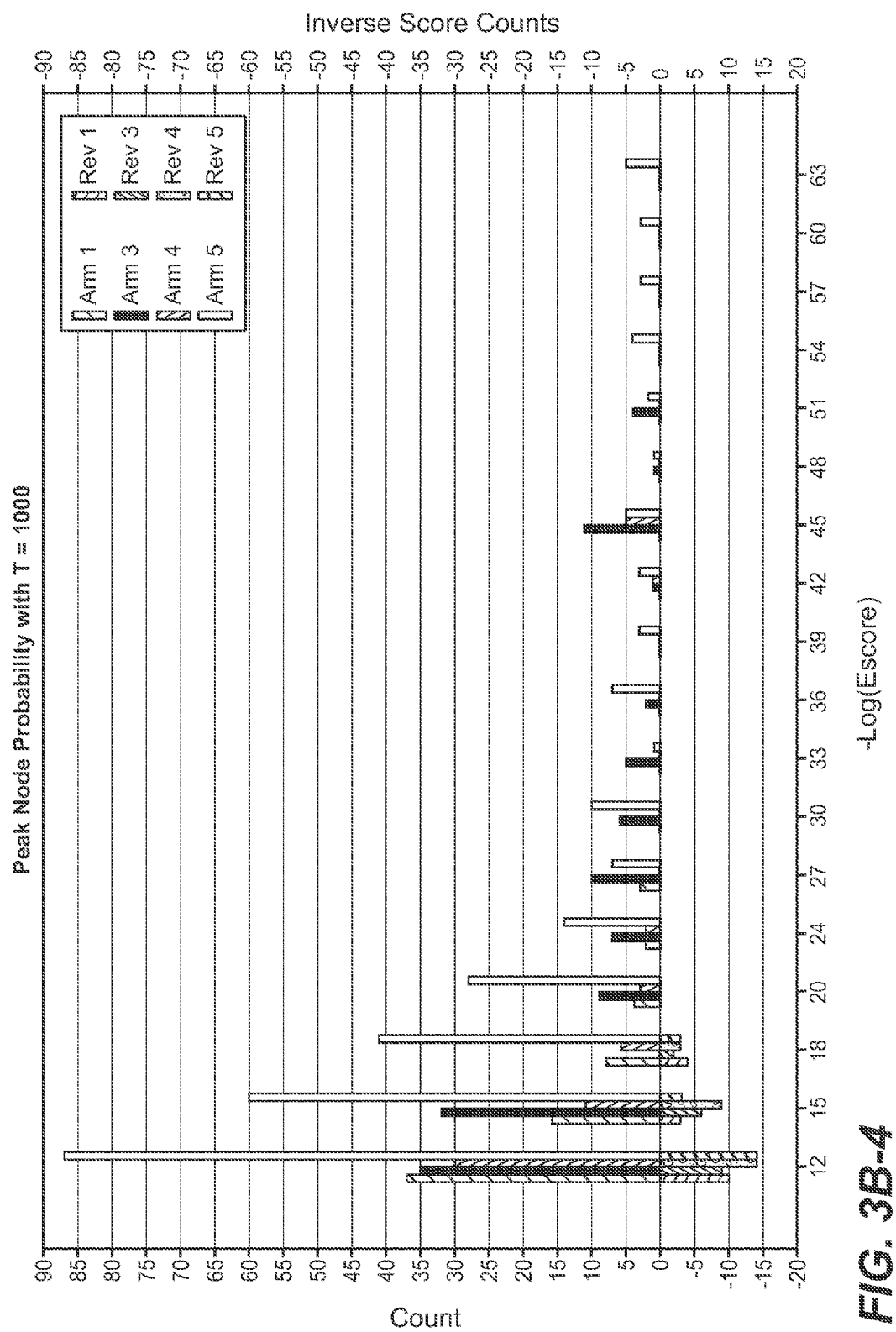
FIG. 4: Light Chain Pairing to Heavy Chain Sequence Library. This figure shows a method for pairing the heavy chain sequences with candidate light chain sequences in order to generate full length antibodies which are then expressed and screened for desired properties. The candidate light chain sequences can either be generated in a similar manner as the heavy chain candidate sequences, or deduced on the basis of isotypes that are known to frequently be paired with and to stabilize the isotype of the heavy chain candidate list.
Figure 4:
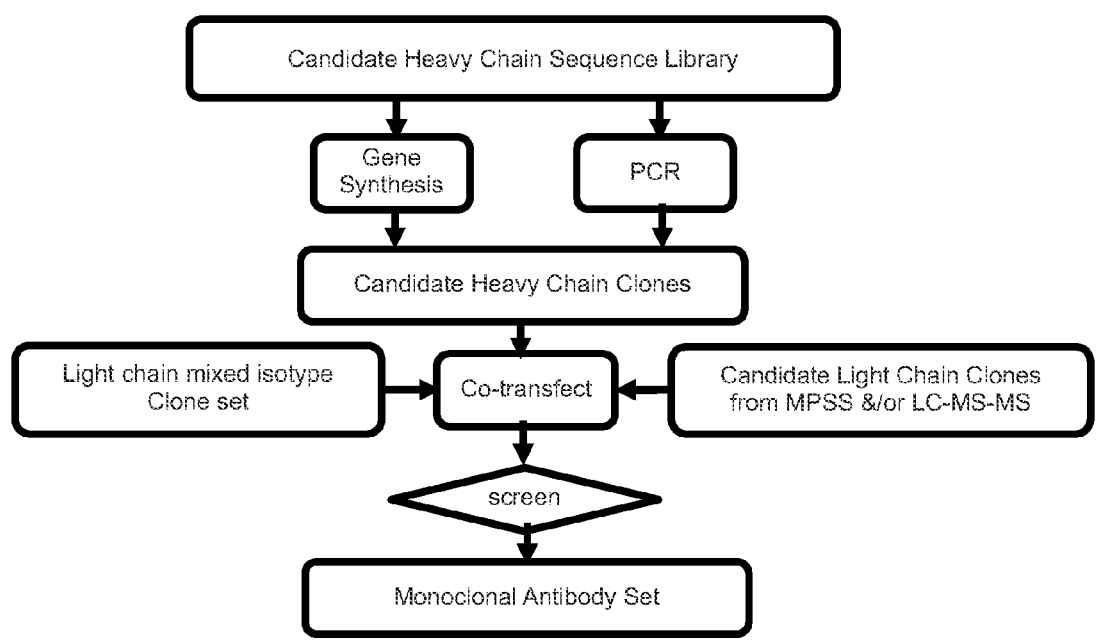

Antibodies are paired dimers of heavy and light chain proteins. Therefore, in order to create a full monoclonal antibody, a light chain must be matched to the heavy chain. FIG. 4 illustrates several methods which can be used to accomplish this. Since light chains primarily contribute stability of binding to the antibody but not antigen specificity, candidate antigen specific heavy chains can be co-transfected with a limited set of light chain antibodies which can then be tested for binding against the target antigen. The set of light chain clones can be biased based on the isotype of the candidate heavy chain clones, since it is known that certain light chain isotypes are more likely than others to form stable high-affinity antibodies when combined with certain heavy chain isotypes. Efficient searching for a suitable light chain can be accomplished by co-transfection of multiple light chain clones with a single heavy chain, testing for antigen binding and once a high affinity antibody is found, deconvoluting the set of light chains with a second set of transfections with each of the light chains alone with the heavy chain.

Additionally one can perform MPSS on light chain sequences in the same manner as described above for heavy chain sequences. This would provide a set of candidate light chains which can be co-transfected with heavy chain sequences alone or in multiplexed combinations in order to find an optimal heavy and light chain pair. This would have the advantage of utilizing native light chain sequences specific for a particular adaptive immune state of an organism.

All of the data from each time point is desirable but not necessarily required for identification of candidate antibody sequences. The combined data processing algorithm takes into account various incomplete combinations of the data set.

Example 5

Experimental Data set from Vaccinated Mice

Immunization

Mice were injected with a blood stage antigen from malaria in combination with four different adjuvant formulations, i.e., arms 1, 3, 4 and 5 of the experiment. Arm 1 was a base formulation while arms 3 and 5 were supplemented with Glycopyranosyl Lipid Adjuvant (GLA), and arms 4 and 5 were supplemented with Resiquimod (R-848). Each of these agents are agonists of Toll-Like Receptors (TLR). In addition samples from a naive control arm was harvested at each time point. Mice were given an initial injection followed by a primary boost at three weeks and a secondary boost at six weeks. cDNA samples were made from circulating blood cells taken on day 6 post-second boost of the adjuvant-antigen combination, and 4 weeks later from both circulating blood samples and bone marrow samples. Biochemical testing of serum taken post vaccination showed that arms 3 and 5 had the highest titer of antibodies with blocking activity of antigen to the host target protein.

Sequencing Sample Generation

Red blood cells in the samples were removed by osmotic lysis followed by washing in PBS. The remaining cells were lysed and used for cDNA synthesis onto oligo-dT coated magnetic beads. The polymerase used was SuperScript III, a highly processive engineered form of reverse transcriptase. A highly processive polymerase master mix, phusion flash, was used for the thermal cycling of the samples. These samples were used in six rounds of synthesis using just upstream primers after which the magnetic cDNA beads were removed by use of a magnetized sample tube holder. Then the 1 µl of the one-way reaction was placed in a 10 µl reaction with both upstream and downstream primers. This mixture was cycled for 18 rounds using a 10 second extension time. Three µl of each of these samples were added to a 30 µl fresh reaction mixture using the same primers and then cycled for an additional 18 rounds.

Primer Sets

PCR primer sets were designed to cover the Ig heavy chain locus of the mouse. First, a list of intact V region sequences with appropriate in-frame leader sequences was created by cross-referencing the Genbank record of the locus with references from the IMGT database. Upstream primer sets were designed to cover the list of V region. By combining together primer sets with a common 3' six base sequence, six pools of forward V region primers were created to cover the entire set of V regions. Two sets of reverse sequence primers were used, a single sequence which was sufficient to cover IgM constant region transcripts and a set of 3 needed to cover the IgG constant isotypes. The IgG reverse primers were also designed with identical 3' six base sequences, and used together in a single pool. The 5' most 8 bases of the primers were designed with a four letter bar-code on the 3' side. The combinations of the barcodes on the forward and reverse primers used on each sample was unique and enables identification of which sample the sequence was derived from. Final PCR reactions programmed from the same cDNA were pooled, and DNA was recovered using a Quiagen PCR cleanup column. The concentration of DNA in each sample was determined from 260/280 OD measurements and the samples were then mixed with equals amounts of DNA from each. This sample was used for library generation and sequencing using the Titanium 454 process.

The results shown in FIG. 3B was obtained by performing a run in a half-plate format and filtered to consider only IgG sequences.

Some portions of above description describe the aspects in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules can be embodied in software, firmware, hardware, or any combinations thereof.

All publications and patent applications cited in this specification are herein incorporated by reference in their entirety for all purposes as if each individual publication or patent application were specifically and individually indicated to be incorporated by reference for all purposes.

Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

What is claimed is:

1. A method, comprising:
   generating a first cDNA sequence library comprising a first set of target antibody cDNA sequences, said first set of target antibody cDNA sequences obtained from a first sample comprising lymphocytes of a host subject that has not been immunized with an antigen and each of said first set of target antibody cDNA sequences comprising an immunoglobulin (Ig) heavy chain variable domain sequence, wherein generating said first cDNA sequence library comprises amplifying said first set of target cDNA sequences and sequencing said amplified first set of target cDNA sequences;

generating a second cDNA sequence library comprising a second set of target antibody cDNA sequences, said second set of target antibody cDNA sequences obtained from a second sample comprising lymphocytes of said host subject after being immunized with said antigen and each of said second set of target antibody cDNA sequences comprising an immunoglobulin (Ig) heavy chain variable domain sequence, wherein generating said second cDNA sequence library comprises amplifying said second set of target cDNA sequences and sequencing said amplified second set of target cDNA sequences;

analyzing the frequencies of occurrence of each of said first and second set of target antibody cDNA sequences;

identifying candidate antibody cDNA sequences that have a statistically significantly higher frequency of occurrence in said second set of target antibody cDNA sequences compared to a frequency of occurrence of said first set of target antibody cDNA sequences;

selecting said candidate antibody cDNA sequences for generating monoclonal antibodies; and expressing said candidate antibody cDNA sequences to produce a plurality of candidate monoclonal antibodies.

2. The method of claim 1, wherein the lymphocytes comprise isolated B cells.

3. The method of claim 1, wherein expressing said candidate antibody cDNA sequences to produce a plurality of candidate monoclonal antibodies comprises subcloning said candidate antibody sequences with a light chain variable domain sequence and an Ig framework.

4. The method of claim 3, wherein the Ig framework is a human Ig framework.

5. The method of claim 3, further comprising assaying the candidate monoclonal antibodies for affinity to the antigen.

6. The method of claim 3, further comprising subjecting the plurality of candidate monoclonal antibodies to positive selection to identify one or more high affinity monoclonal antibodies.

7. The method of claim 6, wherein subjecting the plurality of candidate monoclonal antibodies to positive selection comprises contacting the plurality of candidate monoclonal antibodies to the antigen bound to a substrate and isolating bound antibodies from unbound antibodies.

8. The method of claim 6, wherein the candidate monoclonal antibodies bind to an antigen with an affinity of at least $1\times10^{10}$ liter/mole, measured as an association constant ($K_{aff}$).

9. The method of claim 6, further comprising sequencing the high affinity monoclonal antibodies.

10. The method of claim 1, wherein the frequencies of occurrence of said first and second set of target antibody cDNA sequences are analyzed using a bioinformatics software algorithm.

11. The method of claim 1, wherein the first and second set of target antibody cDNA sequences of said first and second cDNA sequence libraries are sequenced by massively parallel signature sequencing (MPSS).

12. The method of claim 1, wherein the host subject is an experimental animal.

13. The method of claim 1, wherein the host subject is a transgenic animal expressing human antibodies.

14. The method of claim 1, wherein the host subject is a human.

15. The method of claim 1, wherein generating said first or second cDNA sequence library comprises:
i) isolating lymphocytes from the host subject;
ii) isolating mRNA from the lymphocytes; and
iii) reverse transcribing the mRNA to cDNA.

* * * * *